US011116596B2

(12) United States Patent
Stevens

(10) Patent No.: US 11,116,596 B2
(45) Date of Patent: Sep. 14, 2021

(54) SURGICAL SPONGE INVENTORY RACK

(71) Applicant: David G. Stevens, Topeka, KS (US)

(72) Inventor: David G. Stevens, Topeka, KS (US)

(*) Notice: Subject to any disclaimer, the term of this patent is extended or adjusted under 35 U.S.C. 154(b) by 0 days.

(21) Appl. No.: 16/995,297

(22) Filed: Aug. 17, 2020

(65) Prior Publication Data
US 2021/0068914 A1      Mar. 11, 2021

Related U.S. Application Data

(63) Continuation-in-part of application No. 16/564,201, filed on Sep. 9, 2019, now abandoned.

(51) Int. Cl.
| | |
|---|---|
| *A61B 50/22* | (2016.01) |
| *A61B 50/37* | (2016.01) |
| *A47F 5/04* | (2006.01) |
| *A47F 9/04* | (2006.01) |
| *A47F 5/10* | (2006.01) |
| *A61F 13/36* | (2006.01) |

(Continued)

(52) U.S. Cl.
CPC .............. *A61B 50/22* (2016.02); *A47F 5/04* (2013.01); *A47F 5/10* (2013.01); *A47F 9/042* (2013.01); *A61B 50/37* (2016.02); *A47B 43/00* (2013.01); *A61F 13/36* (2013.01); *A61F 15/001* (2013.01)

(58) Field of Classification Search
CPC ......... A61B 50/22; A61B 50/37; A61F 13/36; A61F 50/37; A61F 2050/318; A61F 2050/375; A61F 15/001; A47B 61/02; A47B 43/00; A47B 61/003; A47B 57/583; F16M 11/38; F16M 13/022; F16M 11/121; A47F 7/0042; A47F 13/085; A47F 5/04; A47F 5/10; A47F 5/05; A47F 5/06; A47F 9/042; A47G 25/0685; D06F 57/04
USPC .............. 211/1.3, 85.13, 196, 197, 205, 124, 211/105.3, 106.01, 85.105, 12, 100, 104, 211/175, 172, 171, 195, 105, 202; 248/158, 159, 277.1, 279.1, 274.1, 276.1, 248/294.1, 286.1, 288.11, 291.1, 298.1
See application file for complete search history.

(56) References Cited

U.S. PATENT DOCUMENTS

| | | | | |
|---|---|---|---|---|
| 823,807 | A * | 6/1906 | Peters | ................ A47G 25/0685 |
| | | | | 211/96 |
| 1,005,820 | A * | 10/1911 | Essex | ........................ A47F 5/01 |
| | | | | 211/49.1 |

(Continued)

*Primary Examiner* — Jennifer E. Novosad
(74) *Attorney, Agent, or Firm* — Hovey Williams LLP

(57) ABSTRACT

A surgical sponge inventory rack includes a vertical mounting rod, a laterally extending sponge bag holder connected to the mounting rod, and a sponge bag supported on the sponge bag holder. The sponge bag includes a pocket configured to receive and display a surgical sponge. The sponge bag holder including a plurality of support members. The support members are shiftable relative to one another to transition the sponge bag holder between a collapsed configuration and an expanded configuration. At least one of the support members extends in the lateral direction past another of the support members when the sponge bag holder is in the expanded configuration. The support members collectively present a depth in a fore-and-aft direction that is transverse to the lateral direction and transverse to the vertical direction. The depth is at least substantially constant as the sponge bag holder transitions between the collapsed and expanded configurations.

19 Claims, 23 Drawing Sheets

(51) Int. Cl.
*A61F 15/00* (2006.01)
*A47B 43/00* (2006.01)

(56) References Cited

U.S. PATENT DOCUMENTS

| | | | | |
|---|---|---|---|---|
| 1,073,763 A * | 9/1913 | Kalitzky | A47G 25/0664 | 211/196 |
| 1,188,921 A * | 6/1916 | Finkelstein | A47G 25/0671 | 223/90 |
| 1,447,741 A * | 3/1923 | Vandeventer | A47G 25/403 | 211/104 |
| 1,602,957 A * | 10/1926 | Weigel | A45D 29/18 | 132/314 |
| 1,957,353 A * | 5/1934 | Piersall | A47J 47/20 | 248/212 |
| 2,151,877 A * | 3/1939 | Walker | F16M 11/10 | 248/123.2 |
| 2,311,932 A * | 2/1943 | Deckard | E21B 19/14 | 211/70.4 |
| 2,561,806 A * | 7/1951 | Mailland | A47J 47/16 | 211/96 |
| 2,604,214 A * | 7/1952 | Fussell | A47G 25/0664 | 211/207 |
| 2,630,922 A * | 3/1953 | Hess | A47F 5/04 | 108/28 |
| 2,642,194 A * | 6/1953 | Boltauzer | A47G 25/746 | 211/104 |
| 2,654,484 A * | 10/1953 | Win | A47G 25/08 | 211/1.3 |
| 3,023,912 A * | 3/1962 | Sebastian | D06F 57/04 | 211/196 |
| 3,076,557 A * | 2/1963 | Husted | A45F 3/44 | 211/196 |
| 3,249,233 A * | 5/1966 | Marcus | A47H 1/022 | 211/105.3 |
| 3,380,429 A * | 4/1968 | Moinicken | E01F 13/02 | 116/63 R |
| 3,429,546 A * | 2/1969 | Porter | G09F 7/20 | 248/486 |
| 3,627,244 A * | 12/1971 | Nicholas | A61J 9/0661 | 248/103 |
| 4,029,211 A * | 6/1977 | Marshall | A47B 61/02 | 211/104 |
| 4,428,488 A * | 1/1984 | McAvinn | A61B 50/37 | 211/112 |
| 4,632,255 A * | 12/1986 | Kennedy | A47G 25/0685 | 211/1.3 |
| 4,865,283 A * | 9/1989 | Parker | A47F 5/04 | 248/159 |
| 5,022,538 A * | 6/1991 | Richmond | A47F 5/0876 | 211/107 |
| 5,038,946 A * | 8/1991 | Tenser | A47F 5/04 | 211/168 |
| 5,678,794 A * | 10/1997 | Kump | A47F 5/0869 | 211/59.1 |
| 5,680,943 A * | 10/1997 | Robley | A47B 61/00 | 211/171 |
| 5,692,615 A * | 12/1997 | Fischer | A61B 50/37 | 206/440 |
| 5,732,833 A * | 3/1998 | Alvarado | A47F 9/042 | 206/554 |
| 6,196,398 B1 * | 3/2001 | Lowe | A47B 61/003 | 211/87.01 |
| 6,390,311 B1 * | 5/2002 | Belokin | A61B 50/37 | 211/189 |
| 6,494,327 B2 * | 12/2002 | Huang | A47F 5/0892 | 211/107 |
| 6,607,170 B1 * | 8/2003 | Hoftman | A61B 50/37 | 206/370 |
| 6,698,598 B1 * | 3/2004 | Appenteng | A47F 5/02 | 211/168 |
| 7,143,902 B2 * | 12/2006 | Iversen | A47F 7/24 | 211/123 |
| 7,240,816 B2 * | 7/2007 | Tsai | B60R 9/06 | 211/195 |
| 8,020,716 B2 * | 9/2011 | Vitale | A47F 7/00 | 211/197 |
| 8,047,492 B2 * | 11/2011 | Wang | B62H 3/12 | 248/307 |
| 8,371,457 B2 * | 2/2013 | Entz | A63B 71/0045 | 211/85.7 |
| 8,403,275 B2 * | 3/2013 | Cote | A61M 5/1415 | 248/129 |
| 8,469,206 B2 * | 6/2013 | Wilson | A01M 31/02 | 211/100 |
| 8,540,087 B1 * | 9/2013 | Skaer | A47G 25/0685 | 211/85.3 |
| 8,544,660 B2 * | 10/2013 | Foley | A61B 50/10 | 211/85.15 |
| 8,573,416 B2 * | 11/2013 | Didehvar | A47K 3/281 | 211/119.009 |
| 8,696,057 B2 * | 4/2014 | Wang | B60R 11/02 | 297/188.06 |
| 8,714,369 B2 * | 5/2014 | Liu | A47F 5/10 | 211/27 |
| 8,720,706 B2 * | 5/2014 | Robbins, III | A47F 5/02 | 211/163 |
| 9,198,727 B1 * | 12/2015 | Samuels | A61B 50/10 | |
| 10,383,697 B2 * | 8/2019 | Karasina | A61B 50/26 | |
| 2003/0089830 A1 * | 5/2003 | Loughman | A47F 5/04 | 248/125.7 |
| 2008/0029416 A1 * | 2/2008 | Paxton | A61B 50/20 | 206/370 |
| 2012/0018107 A1 * | 1/2012 | Howery | E21F 1/14 | 160/330 |
| 2015/0233639 A1 * | 8/2015 | Mustari | A47B 96/1425 | 211/101 |
| 2015/0328397 A1 * | 11/2015 | Bally | A47F 5/05 | 211/85.13 |
| 2021/0052342 A1 * | 2/2021 | Rosinski | A61B 90/39 | |

* cited by examiner

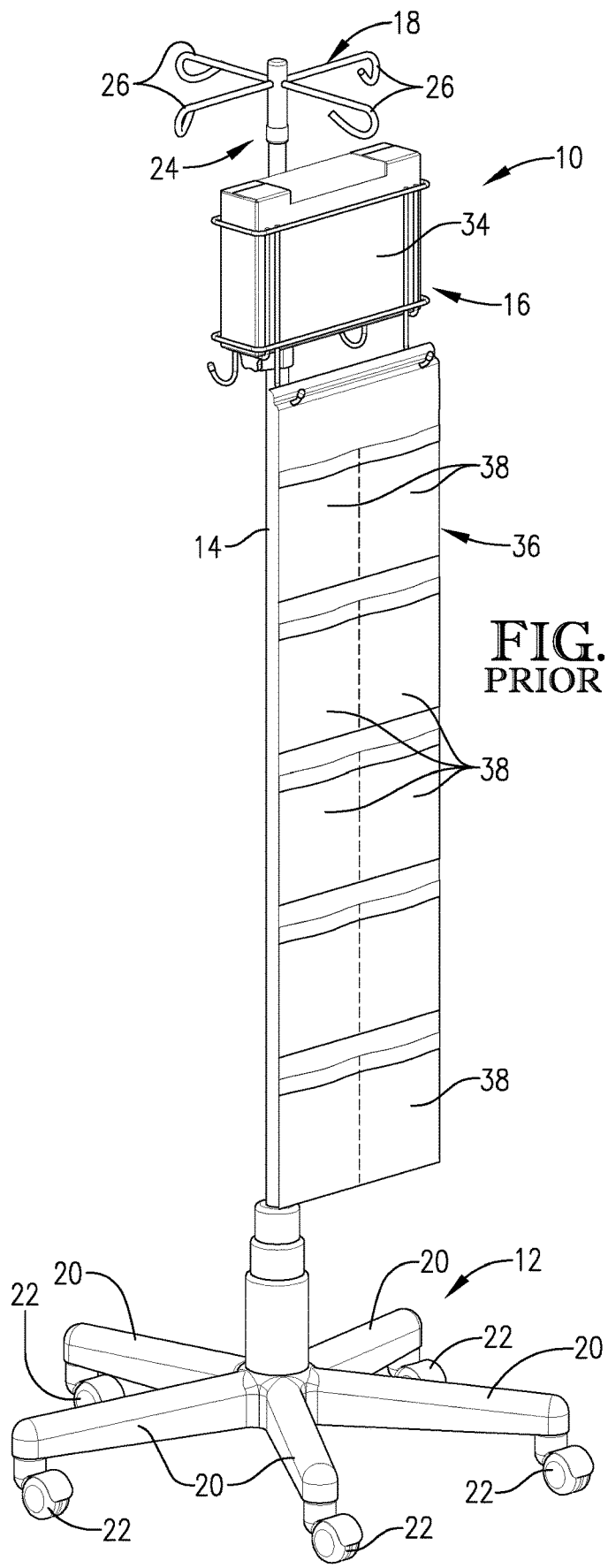
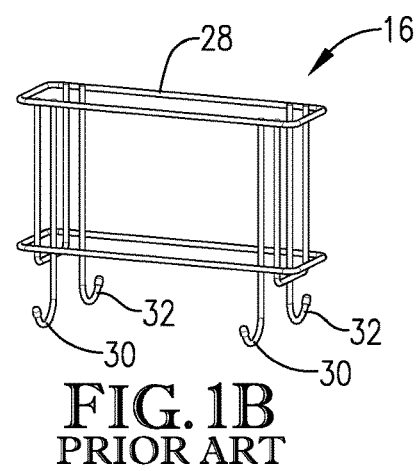
FIG. 1A PRIOR ART
FIG. 1B PRIOR ART

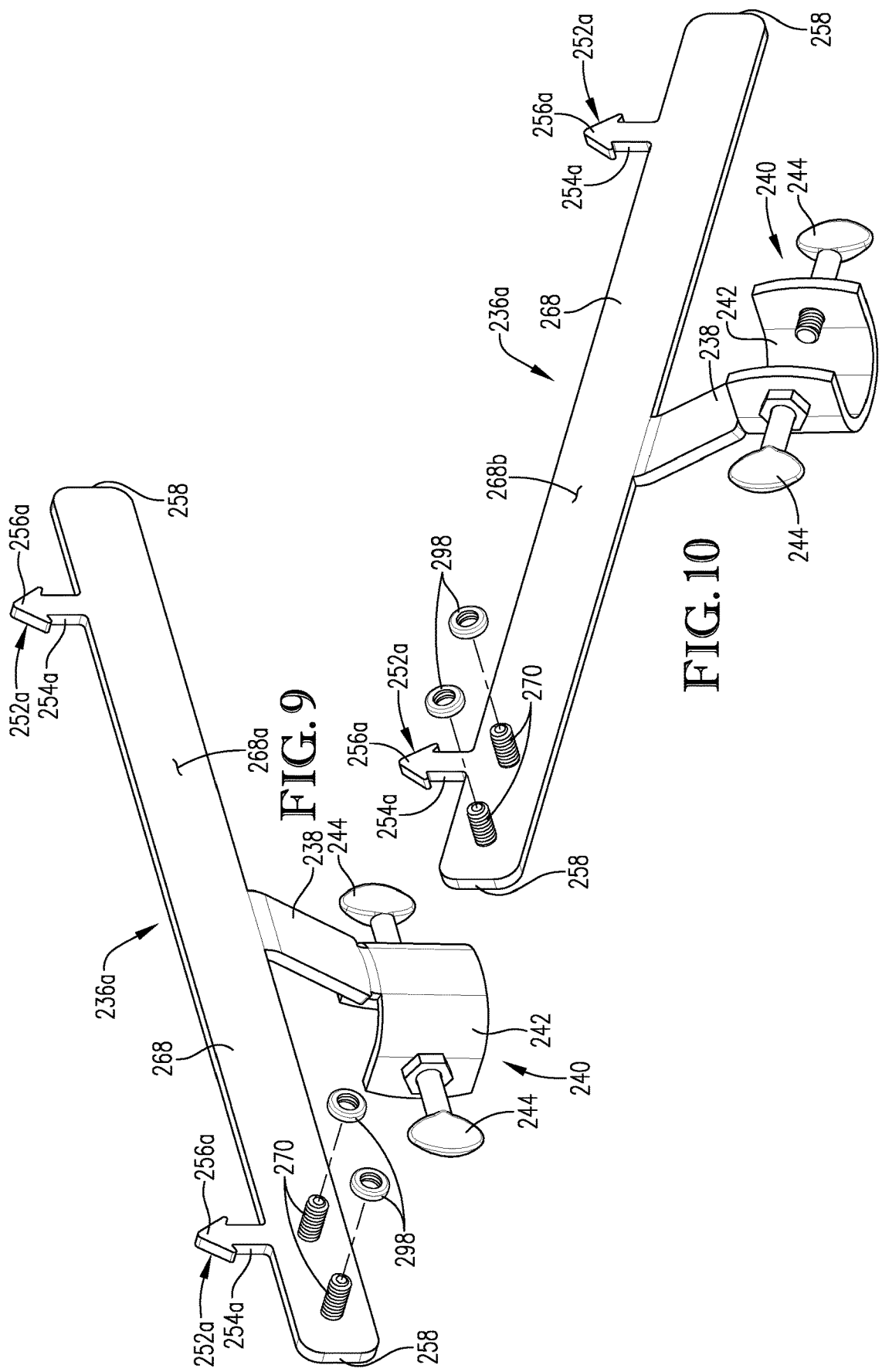

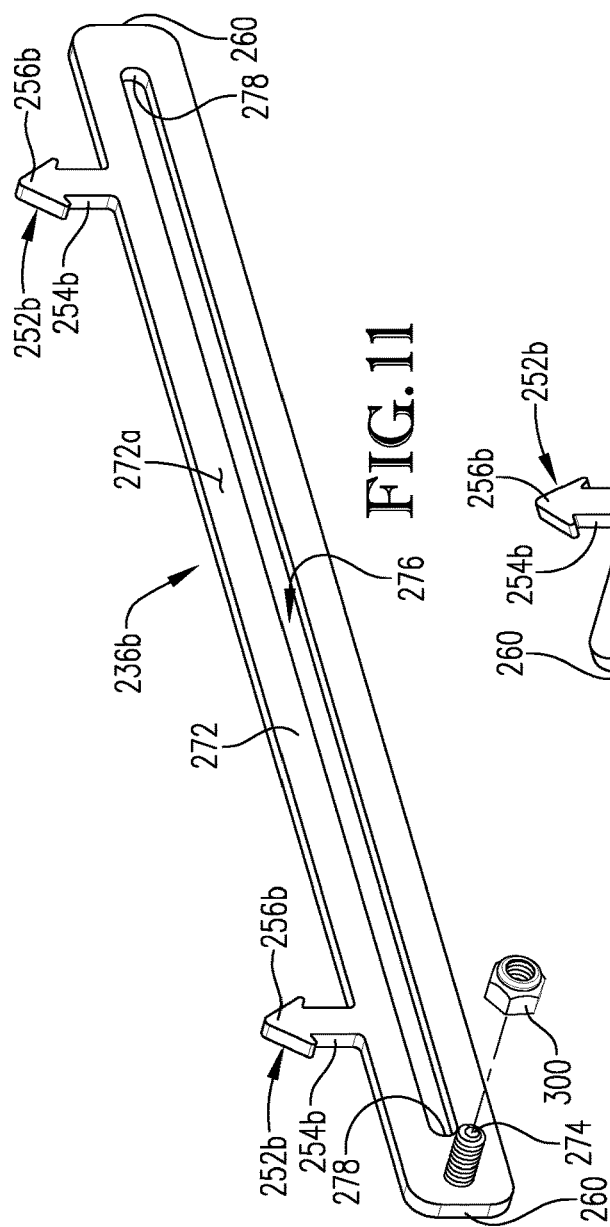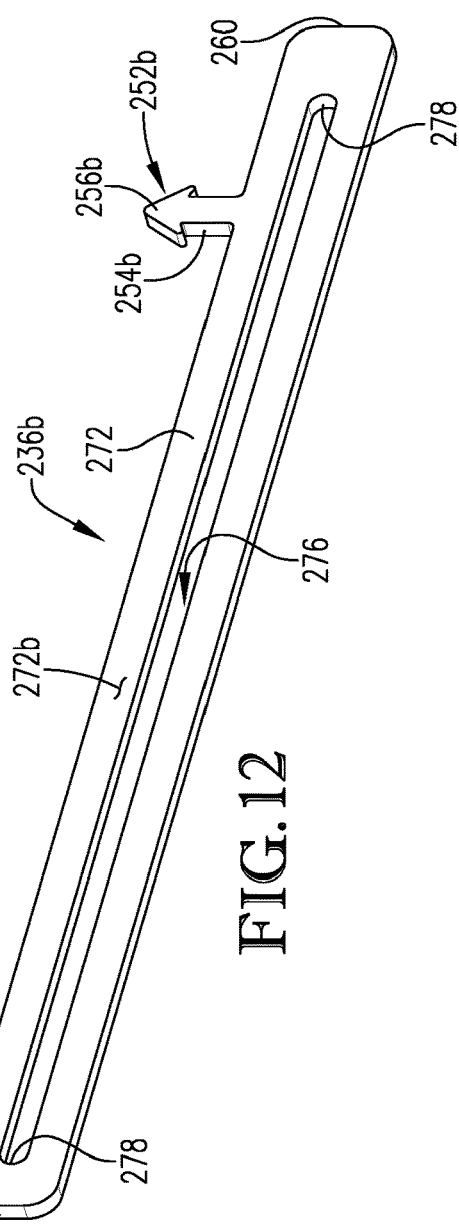

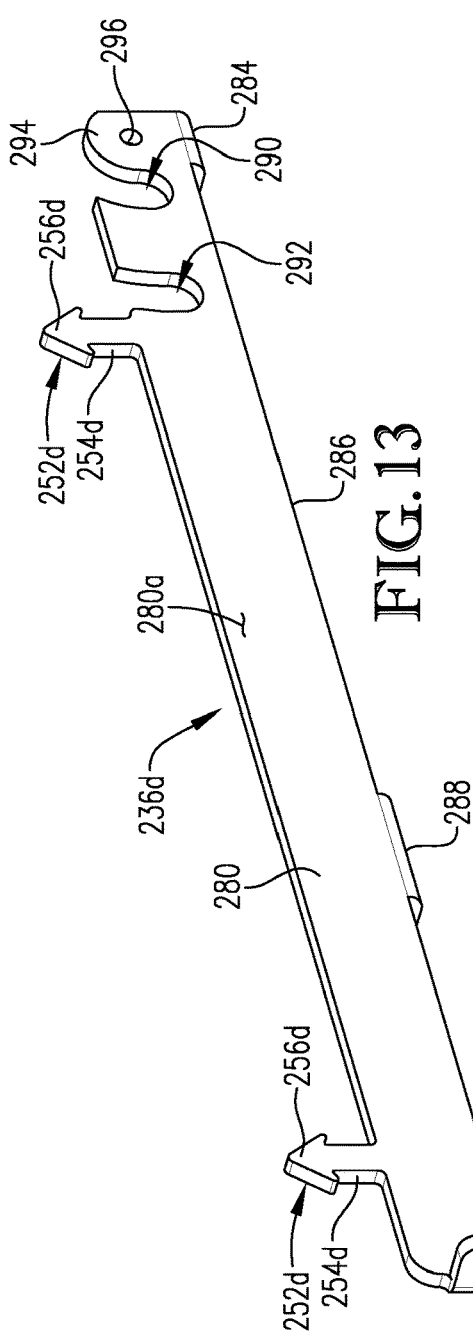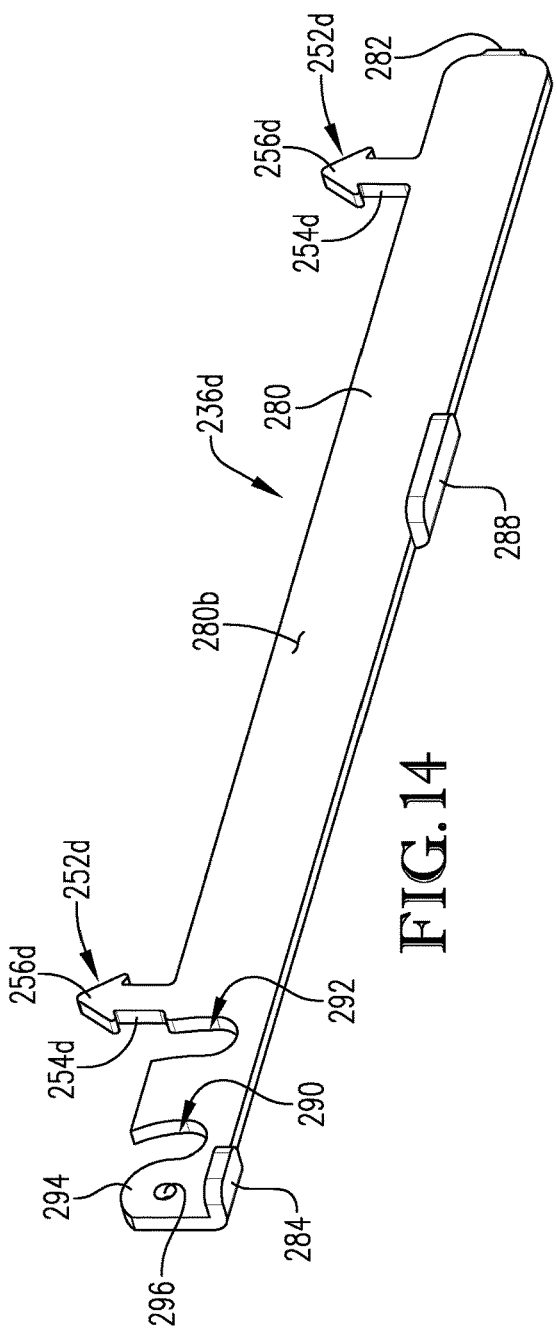

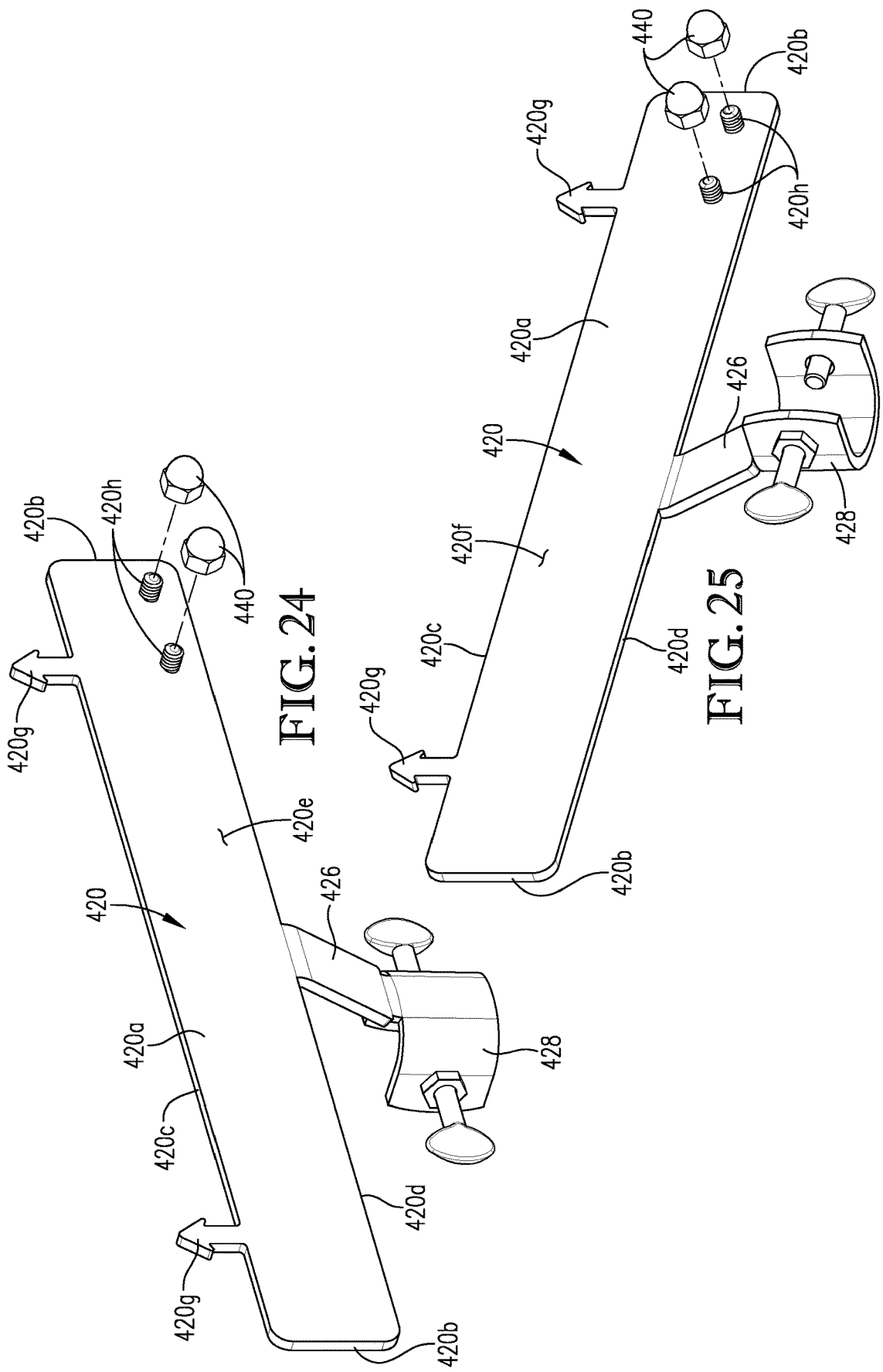

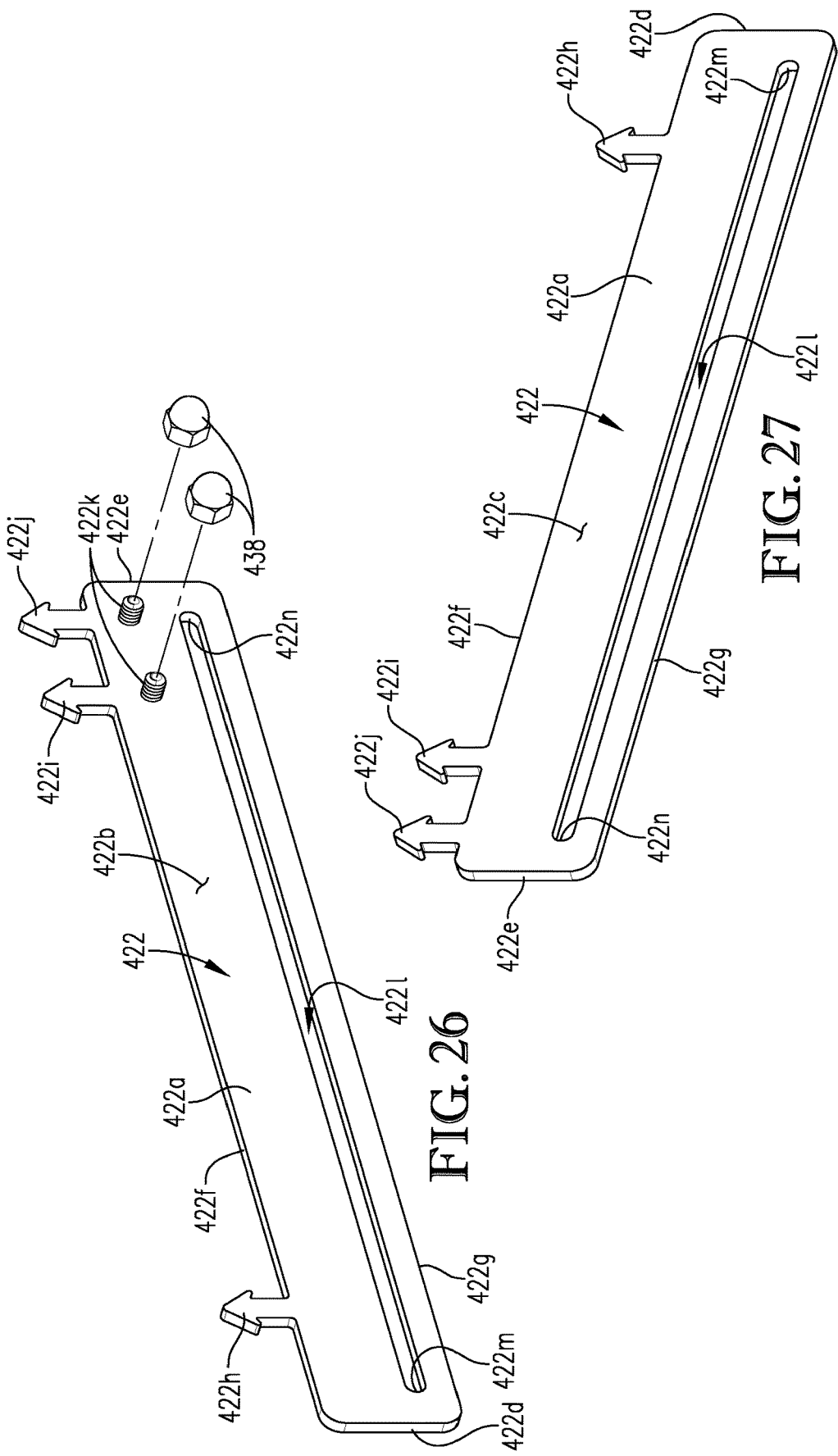

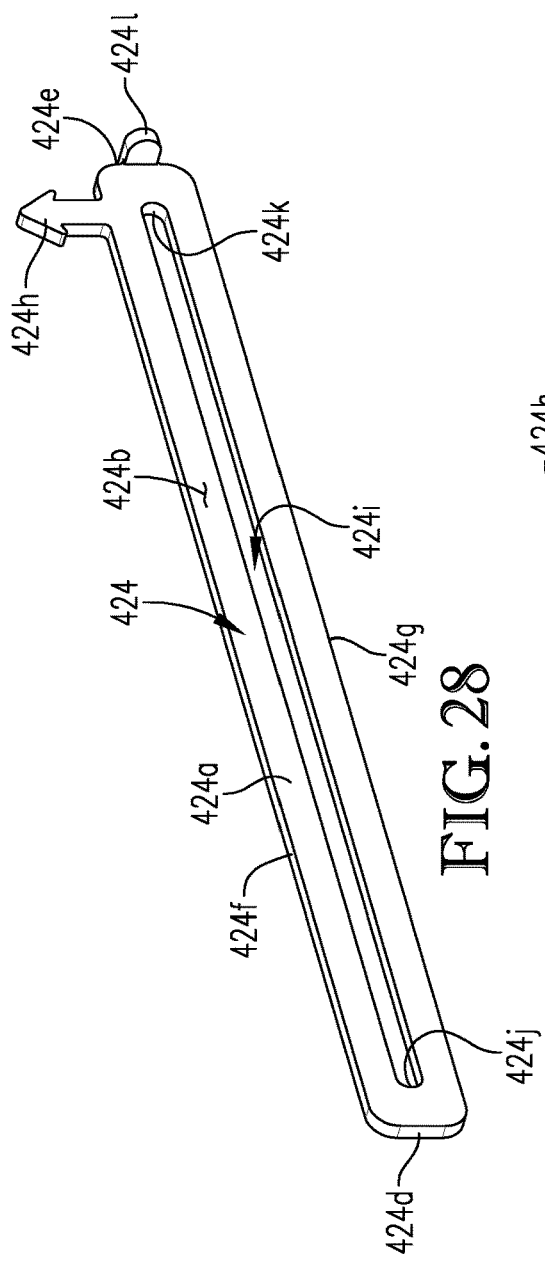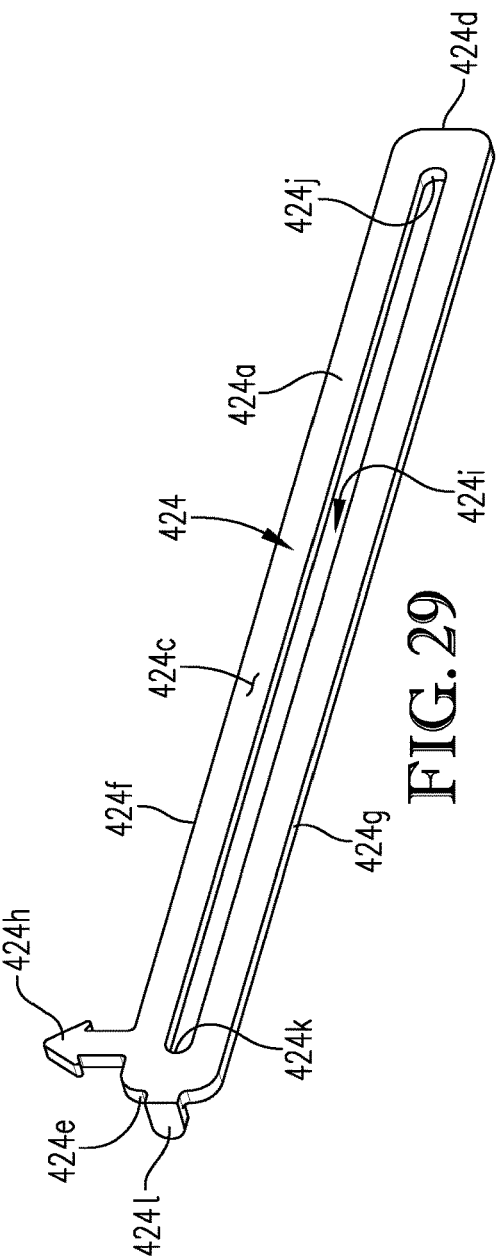

SURGICAL SPONGE INVENTORY RACK

CROSS-REFERENCE TO RELATED APPLICATION

1. Priority Application

The present application is a continuation-in-part of U.S. patent application Ser. No. 16/564,201, filed Sep. 9, 2019, the entire disclosure of which is hereby incorporated by reference herein.

BACKGROUND OF THE INVENTION

1. Field of the Invention

The present invention relates generally to a surgical sponge inventory rack. Such a rack is conventionally used by a member of a surgical team to visually account for all surgical sponges used during a surgical procedure.

2. Discussion of the Prior Art

Those of ordinary skill in the art will appreciate that surgical sponge inventory racks provide a simple visual means of accounting for surgical sponges before, during, and/or after a surgical procedure is performed. Sponge counts may occur prior to a procedure to determine an initial baseline count, at one or more points during a procedure (e.g., prior to closure of a cavity within a cavity), just prior to the final step of the procedure (e.g., just prior to skin closure), and/or as part of relief procedures of a member of a surgical team (e.g., during a shift change for an attending surgical nurse).

Due to space constraints within often crowded operating rooms, surgical sponge inventory racks conventionally present limited width and depth dimensions. As a result, the number of readily visible sponges is often severely limited. More particularly, used sponges are conventionally placed in "sponge counter bags" comprising a plurality of transparent or translucent pockets attached to a flat sheet. If more sponges are necessary for a procedure than can be individually placed in respective ones of the pockets of a single bag, multiple bags must be used. As will be discussed in greater detail below with reference to specific prior art embodiments, the bags may be placed side by side, on the front and back of the rack, and/or stacked in an overlapping manner, potentially resulting in one or more bags (and in turn, sponges) being obscured from view unless additional steps are taken to expose them during each sponge count. Such steps may be time-consuming and increase the potential for erroneous counts.

SUMMARY

According to one aspect of the present invention, a surgical sponge inventory rack comprises a mounting rod extending in a vertical direction, a sponge bag holder connected to the mounting rod and projecting relative thereto in a lateral direction that is transverse to the vertical direction, and a sponge bag supported on the sponge bag holder and including a pocket configured to receive and display a surgical sponge. The sponge bag holder includes a plurality of support members. The support members are shiftable relative to one another to transition the sponge bag holder between a collapsed configuration and an expanded configuration. At least one of the support members extends in the lateral direction past another of the support members when the sponge bag holder is in the expanded configuration. The support members collectively present a depth in a fore-and-aft direction that is transverse to the lateral direction and transverse to the vertical direction. The depth is at least substantially constant as the sponge bag holder transitions between the collapsed configuration and the expanded configuration.

According to another aspect of the present invention, a method of storing and displaying used surgical sponges on a surgical sponge inventory rack is provided. The surgical sponge inventory rack includes a mounting rod extending in a vertical direction and a sponge bag holder connected to the mounting rod. The sponge bag holder includes a plurality of support members. The method comprises the steps of: (a) shifting the support members relative to one another in a lateral direction that is transverse to the vertical direction, such that at least one of the support members extends in the lateral direction past another of the support members, to transition the sponge bag holder from a collapsed configuration to an expanded configuration; (b) hanging a sponge bag from one of said support members such that a pocket of the sponge bag is visible on a front side of the surgical sponge inventory rack; and (c) placing a used sponge into said pocket such that the used sponge is visible from the front side of the surgical sponge inventory rack.

According to yet another aspect of the present invention, a bag holder for use in a surgical sponge inventory rack includes a vertical mounting rod. The bag holder is connectable to the mounting rod and is configured to support sponge bags in which one or more surgical sponges are held. The bag holder comprises a plurality of support members each configured to support a sponge bag thereon. The support members are shiftable relative to one another so as to transition the bag holder between a collapsed configuration and an expanded configuration. At least one of the support members extends in a lateral direction past another of said support members when the bag holder is in the expanded configuration. The support members collectively present a depth in a fore-and-aft direction that is transverse to the lateral direction. The depth is at least substantially constant as the bag holder transitions between the collapsed and expanded configurations. A second one of the support members is slidably intercoupled with a first one of the support members. A third one of the support members is pivotable relative to the second one of the support members. A fourth one of the support members is slidably intercoupled with the first one of the support members. The first one of the support members is disposed laterally between the second one of the support members and the fourth one of the support members when the bag holder is in the expanded configuration.

BRIEF DESCRIPTION OF THE DRAWING FIGURES

Preferred embodiments of the present invention are described in detail below with reference to the attached drawing figures, wherein:

FIG. 1A is a front perspective view of a first prior art surgical sponge inventory rack, including a set of front bag hooks and a set of back bag hooks;

FIG. 1B is an alternate front perspective view of the bag holder of the rack of FIG. 1A;

FIG. 9 is an enlarged front perspective view of the foundational support member of the rack of FIGS. 1-8;

FIG. 10 is a rear perspective view of the foundational support member of FIG. 9;

FIG. 11 is an enlarged front perspective view of one of the intermediate support members of the rack of FIGS. 1-8;

FIG. 12 is a rear perspective view of the intermediate support member of FIG. 11;

FIG. 13 is an enlarged front perspective view of one of the distal support members of the rack of FIGS. 1-8;

FIG. 14 is a rear perspective view of the distal support member of FIG. 13;

FIG. 24 is an enlarged front perspective view of the foundational support member of the rack of FIGS. 20-23;

FIG. 25 is a rear perspective view of the foundational support member of FIG. 24;

FIG. 26 is an enlarged front perspective view of one of the intermediate support members of the rack of FIGS. 20-23;

FIG. 27 is a rear perspective view of the intermediate support member of FIG. 26;

FIG. 28 is an enlarged front perspective view of one of the distal support members of the rack of FIGS. 20-23; and FIG. 29 is a rear perspective view of the distal support member of FIG. 28.

Figure 2A:
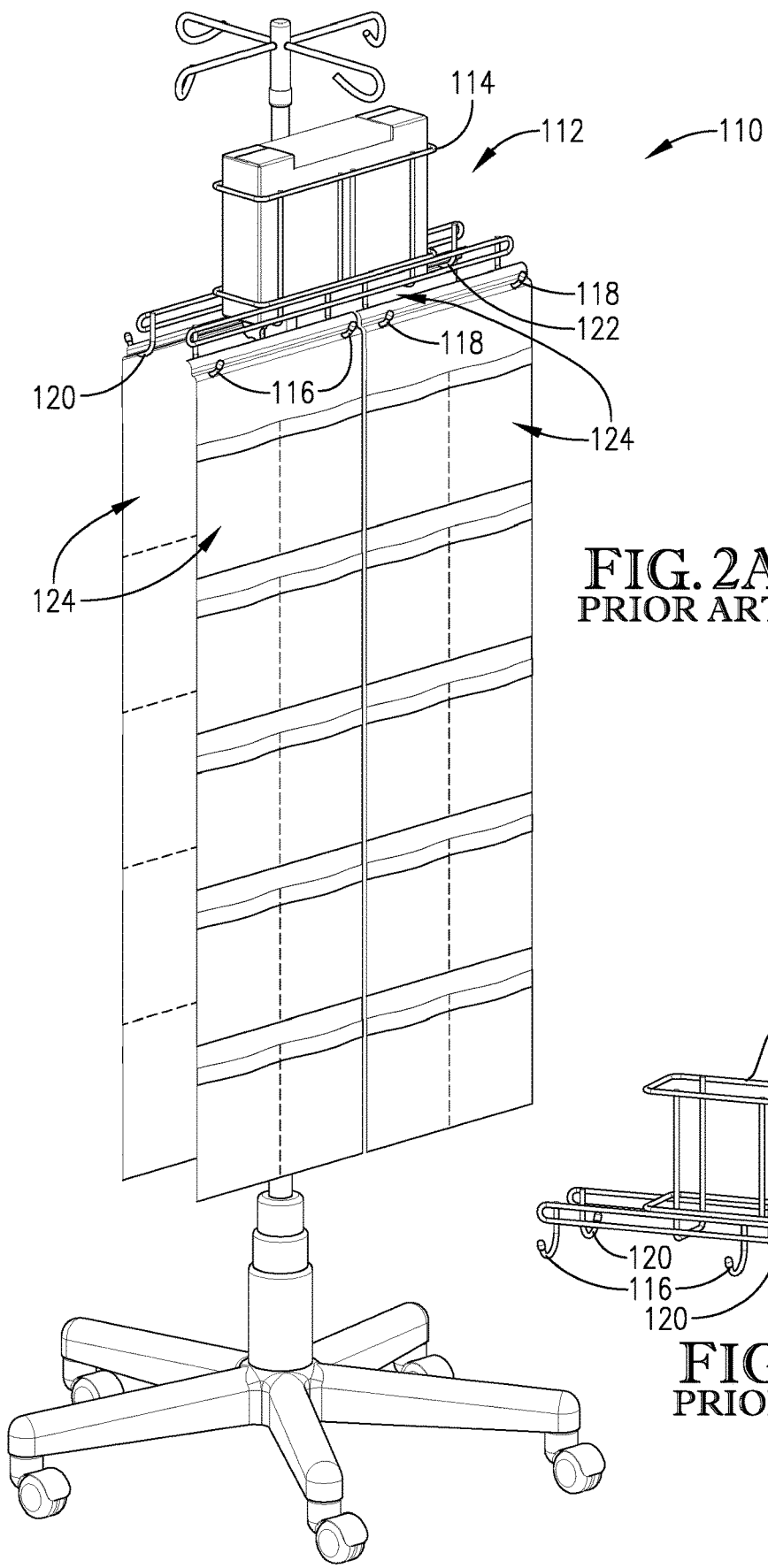
FIG. 2A is a front perspective view of a second prior art surgical sponge inventory rack, including a side-by-side set of front bag hooks and a side-by-side set of rear bag hooks.

The drawing figures do not limit the present invention to the specific embodiments disclosed and described herein. While the drawings do not necessarily provide exact dimensions or tolerances for the illustrated components or structures, the drawings are to scale with respect to the relationships between the components of the structures illustrated in the drawings.

DETAILED DESCRIPTION OF THE PREFERRED EMBODIMENTS

The present invention is susceptible of embodiment in many different forms. While the drawings illustrate, and the specification describes, certain preferred embodiments of the invention, it is to be understood that such disclosure is by way of example only. There is no intent to limit the principles of the present invention to the particular disclosed embodiments.

Furthermore, unless specified or made clear, the directional references made herein with regard to the present invention and/or associated components (e.g., top, bottom, upper, lower, inner, outer etc.) are used solely for the sake of convenience and should be understood only in relation to each other. For instance, a component might in practice be oriented such that faces referred to as "top" and "bottom" are sideways, angled, inverted, etc. relative to the chosen frame of reference.

Conventional Designs

With initial reference to FIGS. 1A and 1B, a prior art surgical sponge inventory rack 10 is illustrated. The rack 10 includes a base 12, a mounting rod 14, a bag holder 16, and a top 18. The base 12 includes a plurality of radially extending legs 20 each supported by a respective caster 22. The casters 22 enabling rolling of the entire rack 10 and thereby facilitate easy positioning of the rack 10. The mounting rod 14 extends vertically upward from the base 12 and is centered relative to the legs 20. The bag holder 16 is fixed to the mounting rod 14. The top 18 is disposed at an upper end 24 of the mounting rod and includes a plurality of radially extending arms 26. Those of ordinary skill in the art will appreciate that the base 12, rod 14, and top 18 cooperatively make up a traditional mobile IV stand.

The bag holder 16 includes a frame 28 and front and rear pairs of bag hooks 30 and 32, respectively. A replaceable package 34 for containment and dispensation of unused surgical sponge bags is supported within the frame 28. A sponge bag 36 hangs from the front bag hooks 30 so as to present ten (10) readily visible pockets 38. The rear bag hooks 32 are shown empty in the illustrated embodiment. However, during the course of a surgical procedure, should the illustrated bag 36 become full of used sponges, a second bag might be hung from the rear hooks 32 to provide additional pockets, and/or bags might be stacked on top of one another (i.e., layered in an overlapping manner). Thus, the illustrated bag 36 might eventually be covered by another bag, making the sponges received in the pockets visible only upon lifting of the overlying bag.

The rack 10 of FIGS. 1A and 1B enables unobstructed visibility of only (10) sponges on each side thereof and only twenty (20) total sponges before overlapping of bags is necessary. Due to space constraints, limited time, and/or other factors, it may be undesirable for surgical staff to be required to walk around the rack 10 to see both front and rear bags in order to count more than ten (10) surgical sponges. Similarly, it may be undesirable to require "flipping through" layers of bags in order to obtain a count of used sponges that exceeds ten (10).

Figure 2B:
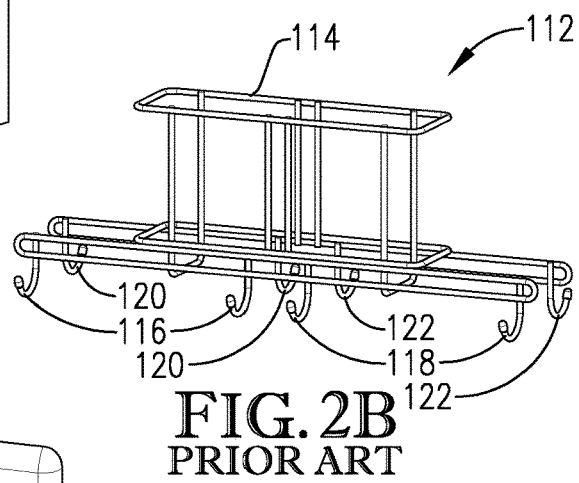
FIG. 2B is an alternate front perspective view of the bag holder of the rack of FIG. 2A.

Turning to FIGS. 2A and 2B, a second prior art sponge inventory rack 110 is illustrated. The second prior art rack 110 differs from the first prior art rack 10 primarily in the configuration of the bag holder 112. More particularly, the bag holder 112 of the rack 110 includes a frame 114, two (2) pairs of front bag hooks 116 and 118, and two (2) pairs of rear bag hooks 120 and 122. Thus, double the number of bags 124 are visible on each side of the rack 110 compared to the rack 10 of the first prior art embodiment, and stacking or overlapping of bags 124 is also necessary only after twice the number of sponges have been used.

Although the rack 110 is an improvement over the rack 10, the deficiencies described above with regard to the rack 10 nevertheless apply.

Design 1: Slidable and Pivotable Flat Plate Support Members

Figure 3:
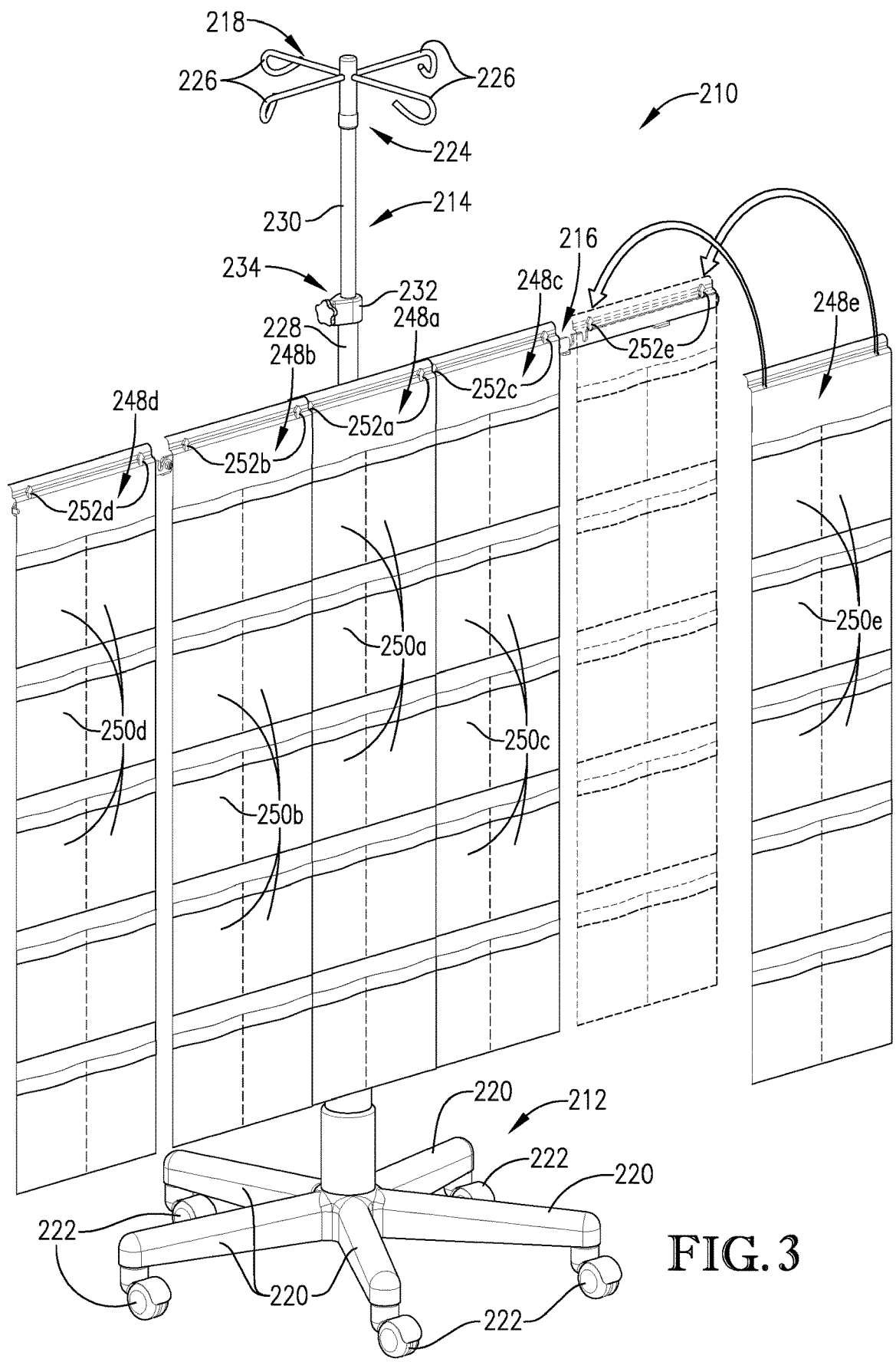
FIG. 3 is a front perspective view of a surgical sponge inventory rack according to a first preferred embodiment of the present invention, particularly illustrating a fully open or expanded configuration.
Figure 4:
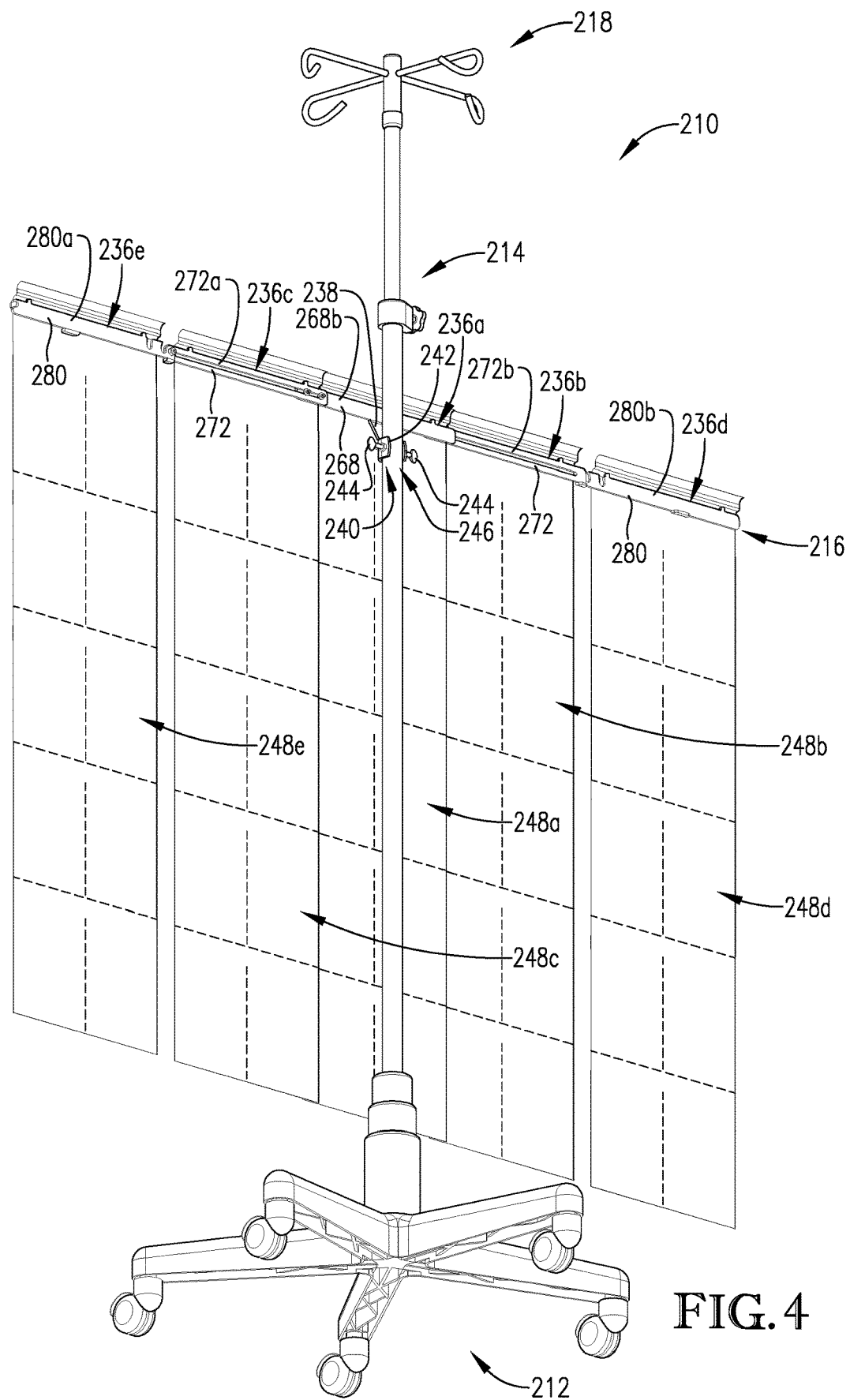
FIG. 4 is a rear perspective view of the rack of FIG. 3.

FIGS. 3 and 4 illustrate front and rear perspective views of a first embodiment of the present invention, in a fully expanded configuration. (Partially expanded/contracted/collapsed and fully contracted/collapsed configurations will be discussed in greater detail below.) More particularly, a surgical sponge inventory rack 210 is provided. The rack 210 includes a base 212, a mounting rod 214, a bag holder 216, and a top 218. As will be discussed in greater detail below, the bag holder 216 is shiftable between fully contracted and fully expanded configurations corresponding to so-called fully contracted and fully expanded configurations of the rack 210 as a whole.

In a preferred embodiment, the base 212, the mounting rod 214, and the top 218 are multi-purpose components capable of playing alternative roles within a medical context. For instance, the illustrated base 212, mounting rod 21, and top 218 are additionally suitable for use as part of a mobile IV pole or stand, etc.

The base 212 includes a plurality of radially extending legs 220 each supported by a respective caster 222. The mounting rod 214 extends at least substantially vertically and most preferably fully vertically upward from the base 212 and is centered relative to the legs 220. That is, the legs 220 each extend radially outwardly from the mounting rod 214. The top 218 is disposed at an upper end 224 of the mounting rod 214 and preferably includes a plurality of radially extending arms 226.

In a preferred embodiment, as illustrated, the rod 214 is a telescoping rod 214 including at least a larger-diameter base member 228 and a smaller-diameter upper member 230. A collar 232 is preferably provided to tighten or loosen a juncture 234 between the members 228 and 230 and to facilitate or restrict, and ultimately at least substantially eliminate, relative axial motion between the members 228 and 230. It is permissible according to some aspects of the present invention, however, for a non-telescoping rod to be provided.

The bag holder 216 preferably includes a plurality of support members 236a-e; a bracket 238 supporting the support members 236a-e; and a clamp 240 supporting the bracket 238. The clamp 240 includes a band 242 at least in part encircling the rod 214 and a pair of adjustable keys 244 extending through the clamp 240 and configured to shift radially inwardly or outwardly to engage or disengage from the rod 214. The keys 244 and the band 242 thereby tighten or loosen a juncture 246 between the bag holder 216 and the rod 214 (and most preferably, the base member 228 thereof) to facilitate or restrict, and ultimately at least substantially eliminate, relative motion between the bag holder 216 and the rod 214. The height of the bag holder 216 can thereby be readily adjusted, and subsequently fixed. Undesirable rotation of the bag holder 216 around the rod 214 is also at least substantially prevented. It is permissible according to some aspects of the present invention, however, for a non-positionally adjustable bag holder to be provided.

The bag holder 216 is preferably formed of metal, although other materials fall within the scope of the present invention.

The bracket 238 preferably extends forward from the rod 214 such that the support members 236a-e are disposed on a front side of the rack 210.

In a preferred embodiment, a plurality of bags 248a-e, each including respective pluralities of pockets 250a-e, hang from respective ones of the support members 236a-e. Most preferably, each of the bags 248a-e hangs from a front side of the rack 210 such that the pockets 250a-e are all visible from a single position (e.g., a vantage point in front of the rack 210). In the illustrated embodiment, for instance, five (5) bags 248a-e, each including ten (10) respective pockets 250a-e, are simultaneously visible from a single position to enable an unobstructed count of up to fifty (50) used sponges, assuming only one sponge is place in each pocket 250a-e.

Preferably, each support member 236a-e includes a respective pair of hooks 252a-e projecting upwardly therefrom when the support members 236a-e are in an expanded configuration. Each hook 252a-e preferably includes a base 254a-e and a head 256a-e, with each head 256a-e restricting slippage of one or more corresponding mounted bags 248a-e off of the corresponding support member 236a-e.

Most preferably, the heads 256a-e are each in the shape of a triangle. The bases 254a-e are each preferably in the shape of rectangle. The hooks 252a-e are therefore generally in the shape of upwardly pointing arrows when the bag holder 216 is in a fully expanded configuration. A variety of hook shapes fall within the scope of the present invention, however.

The support members 236a-e most preferably include a foundational support member 236a, a pair of slidable support members 236b and 236c, and a pair of pivotable support members 236d and 236e.

Thus, five (5) support members 236a-e are provided, with each of the support members 236a-e most preferably configured to display one (1) bag 248a-e in a substantially unobstructed manner.

Configurations that do not achieve one-to-one correspondence between support members and bags are also permissible according to some aspects of the present invention. For instance, one or more of the support members might be configured to cooperatively support a single bag (e.g., a single bag might hang from a first hook provided by first support member and a second hook provided by an adjacent support member). Stacking of bags, as discussed above with regard to the prior art, may also occur; but a substantially complete "top" bag should always remain visible when hanging from its respective support member, when the bag holder (or, in a more general sense, the rack) is in a fully expanded configuration. "Substantially" as used in the present sense should be understood to mean simply that any overlap that occurs between adjacent bags is small enough that any sponges held in said bags are readily visible for easy and unambiguous counting.

Although five (5) support members 236a-e are provided in the illustrated embodiment, it is noted that more or fewer support members may be provided without departing from the scope of some aspects of the present invention.

The foundational support member 236a is preferably centered on the rod 214 so as to extend laterally therefrom, equidistantly in two (2) opposing directions. As will be discussed in greater detail below, the foundational support member 236a as a whole is also preferably radially symmetrical (i.e., formed by a pair of identical halves offset one hundred and eighty (180) degrees from each other). The foundational support member 236a presents opposite longitudinal ends 258.

Figure 5:
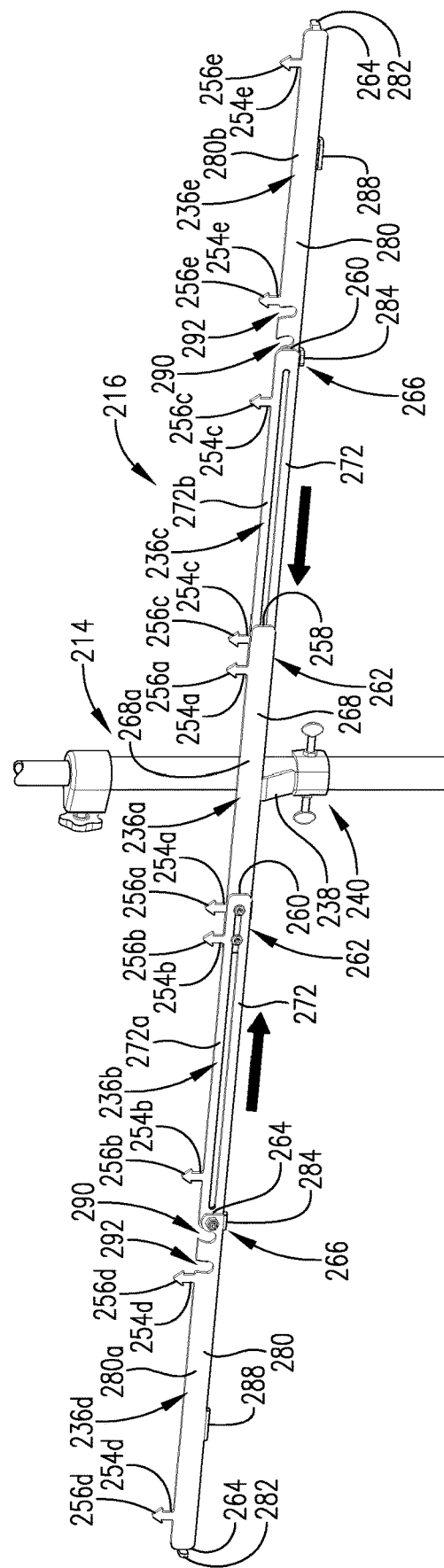
FIG. 5 is an enlarged front perspective view of a portion of the rack of FIG. 4, in a fully open or expanded configuration.

The slidable support members 236b and 236c are preferably identical to each other and each preferably feature mirror symmetry. The slidable support members 236b and 236c each present a pair of longitudinal ends 260. As best shown in FIG. 5, the proximal or inner ones of the ends 260 of each of the slidable support members 236b and 236c preferably each overlap an adjacent one of the ends 258 of the foundational support member 236a when the rack 210 is in the expanded configuration. An overlapping region 262 is thus defined between the support members 236a and 236b, and also between the support members 236a and 236c.

The slidable support members 236b and 236c are preferably oriented so as to collectively (i.e., cooperatively) present radial symmetry. That is, whereas the slidable support member 236b may be interpreted as facing forward, the slidable support member 236c may be interpreted as facing backward.

The pivotable support members 236d and 236e are preferably identical to each other but do not feature mirror symmetry. However, the pivotable support members 236d and 236e are preferably oriented so as to collectively present radial symmetry. That is, whereas the pivotable support member 236d may be interpreted as facing forward, the pivotable support member 236e may be interpreted as facing backward.

The pivotable support members 236d and 236e are preferably the distalmost or outer of the support members 236a-e when the rack 210 is in the expanded configuration. More particularly, each pivotable support member 236d and 236e preferably presents pair of longitudinal ends 264. As best shown in FIG. 5, the proximal or inner ones of the ends 264 of each of the pivotable support members 236d and 236e preferably each overlap an adjacent one of the ends 260 (i.e., a distalmost or outer one of the ends 260) of the adjacent slidable support member 236b or 236c, respectively, when the rack 210 (or, alternatively stated, the bag holder 216) is in the expanded configuration. An overlapping region 266 is thus defined between the support members 236b and 236d, and also between the support members 236c and 236e.

Interaction of the various support members 236a-e will be discussed in greater detail below, after individual structures of the support members 236a-e are further described.

As best shown in FIGS. 9 and 10, the foundational support member 236a preferably includes a laterally extending body 268 presenting the aforementioned ends 258. Each of the hooks 252a preferably projects vertically upward from the body 268 when the rack 210 is in the fully expanded configuration. The hooks 252a are preferably integral with and, more particularly, unitarily formed with, the body 268, although non-integral formation is permissible. The hooks might, for instance, be adhered, latched, welded, or otherwise attached to the body.

The bracket 238 is preferably unitarily formed with the body 268, with the clamp 240 in turn being unitarily formed with the bracket 238. Non-unitary configurations fall within the scope of the present invention, however.

The body 268 is preferably in the general form of a flat plate and presents a front face 268a and a rear or back face 268b. A first pair of laterally spaced apart threaded projections 270 preferably project forward and at least substantially orthogonally from the front face 268a adjacent one of the ends 258. A second pair of laterally spaced apart threaded projections 270 preferably projects backward and at least substantially orthogonally from the rear face 268b adjacent the other one of the ends 258.

As best shown in FIGS. 11 and 12, each of the slidable support members 236b,c preferably includes a laterally extending body 272 presenting the aforementioned first and second ends 260. The corresponding hooks 252b,c preferably project vertically upward from the respective bodies 272 when the rack 210 is in the fully expanded configuration. The hooks 252b,c are preferably integral with and, more particularly, unitarily formed with, the respective ones of the bodies 272, although non-integral formation is permissible. The hooks might, for instance, be adhered, latched, welded, or otherwise attached to the respective body.

Each body 272 preferably is in the general form of a flat plate and presents a front face and a rear face 272b. A first threaded projection 274 preferably projects forward and at least substantially orthogonally from the front face 272a, adjacent the outer or distal one of the ends 260.

It is particularly noted that in the assembled rack 210, the "local" front face 272a of the slidable support member 236b faces forward in a "general" sense (i.e., in the orientation system of the rack 210 as a whole), while the "local" front face 272a of the slidable support member 236c faces rearward in "general" sense. That is, the slidable support members 236b and 236c are oriented oppositely of each other in the assembled rack 210 despite being structurally identical to each other. Thus, the aforementioned collective rotational symmetry of the slidable support members 236b and 236c in the assembled rack 210 is achieved.

A longitudinally extending slot 276 is preferably defined through the body 272 of each slidable support member 236b,c. Each slot 276 presents a pair of ends 278. Each slot defines a longitudinal slot length and a vertical (when the rack 210 is in the fully expanded configuration) slot height. The slot length most preferably approaches a total length of the slidable support member 236b or 236c (e.g., is at least seventy-five percent (75%), is more preferably at least eighty percent (80%), and is most preferably at least ninety percent (90%) of the total length of the slidable support member 236b or 236c), as measured between the corresponding ends 260.

With respect to FIGS. 13 and 14, each pivotable support member 236d and 236e preferably includes a laterally extending body 280 presenting the aforementioned first and second ends 264. The corresponding hooks 252d,e preferably project vertically upward from the respective bodies 280 when the rack 210 is in the fully expanded configuration. The hooks 252d,e are preferably integral with and, more particularly, unitarily formed with, the respective ones of the bodies 280, although non-integral formation is permissible. The hooks might, for instance, be adhered, latched, welded, or otherwise attached to the respective body.

Each body 280 preferably is generally in the form of a flat plate and presents a front face 280a and a rear face 280b. A tab 282 preferably projects forward and at least substantially orthogonally from the front face 280a adjacent the outer one of the ends 264. A proximal lip 284 preferably projects rearward and at least substantially orthogonally to the body 280 from a bottom edge thereof, adjacent the inner or proximal one of the ends 264. The lip 284 therefore projects horizontally when the rack 210 is in the fully expanded configuration. Similarly, an intermediate lip 288 preferably projects rearward and at least substantially orthogonally to the body 280 from the bottom edge 286 thereof, at a position spaced between the ends 264. The lip 288 therefore projects horizontally when the rack 210 is in the fully expanded configuration.

It is particularly noted that in the assembled rack 210, the "local" front face 280a of the pivotable support member 236d faces forward in a "general" sense (i.e., in the orientation system of the rack 210 as a whole), while the "local" front face 280a of the pivotable support member 236e faces rearward in "general" sense. That is, the pivotable support members 236d and 236e are oriented oppositely of each other in the assembled rack 210 despite being structurally identical to each other. Thus, the aforementioned collective rotational symmetry of the pivotable support members 236d and 236e in the assembled rack 210 is achieved.

First and second notches 290 and 292 and are preferably defined through the body 280 of each pivotable support member 236d,e. The notches 290 and 292 each define a respective longitudinal notch width and vertical (when the rack 210 is in the fully expanded configuration) notch depth.

The innermost notch 290 is in part defined in part by a proximally located rounded portion 294 of the body 280. The rounded portion 294 is immediately adjacent the proximal or inner one of the ends 264 and above the proximal lip 284. An opening 296 extends through the rounded portion 294.

FIGS. 3-5 illustrate the rack 210 in its fully expanded configuration. Each pair of projections 270 of the foundational support member 236a extends through the slot 276 of a corresponding one of the slidable support members 236b and 236c. Washers 298 threaded onto the projections 270 clamp the slidable support members 236b and 236c to the foundational support member 236a and restrict lateral sliding of the slidable support members 236b and 236c relative thereto.

As illustrated, in the fully expanded configuration, the slidable support members 236b and 236c are positioned such that the projections 270 are disposed adjacent the inner ends 278 of the corresponding slots 276, such that the length of the overlapping regions 262 are minimized to the extent possible given the geometrical constraints of the support members 236a-c. That is, within the constraints of the geometry of the support members 236a-c, a collective lateral span achieved by the support members 236a-c is maximized.

It is noted that the minimum amount of overlap forming the regions 262 between the foundational support member 236a and the slidable support members 236b and 236c, as dictated by the support member geometries, is preferably sufficient to provide adequate structural rigidity for the support members 236a-c to support one or more bags 248a-c fully loaded with surgical sponges and also to endure bumps, moves, etc. associated with general use in a busy surgical environment.

The projections 274 of the slidable support members 236b and 236c are preferably received in corresponding ones of the openings 296 formed in the rounded portions 294 of the corresponding pivotable support member 236d or 236e, respectively. Nuts 300 threaded onto the projections 274 clamp the pivotable support members 236d and 236e to the corresponding slidable support members 236b and 236c, respectively, and restrict pivoting of the pivotable support members 236b,c relative thereto.

As illustrated, in the fully expanded configuration of the rack 210, each projection 274 is disposed at a laterally outermost one of the ends 260 of the corresponding slidable support member 236b or 236c. Furthermore, the openings 296 are disposed at laterally innermost ones of the ends 264 of the pivotable support members 236d and 236e. Thus, the lengths of the aforementioned overlapping regions 266 are minimized (to the extent possible given the geometrical constraints of the support members 236b-e). That is, within the constraints of the geometry of the support members 236b-e, a collective lateral span achieved by the support members 236b-e is maximized.

Thus, it will be apparent that a collective lateral expanded width or span of all of the support members 236a-e is maximized when the rack 210 is in a fully expanded configuration. The expanded width is preferably between about thirty inches (30") and about seventy inches (70"). More preferably, the expanded width is between about forty inches (40") and about sixty inches (60"). Most preferably, the expanded width is about fifty-one and twenty-five hundredths inches (51.25").

Furthermore, it will be apparent that the support members 236a-e are collectively (i.e., when viewed as a whole) centered relative to the rod 214. More particularly, the bracket 238 is preferably centrally fixed to the foundational support member 236a. The bracket 238 is therefore laterally centered relative to the support members 236a-e in a collective sense both when the bag holder 216 is in the collapsed configuration and when the bag holder 216 is in the expanded configuration. Upon securement of the bracket 238 to the rod 214, the support members 236a-e are therefore likewise collectively centered relative to the rod 214 both when the bag holder 216 is in the collapsed configuration and when the bag holder 216 is in the expanded configuration.

Still further, the support members 236a-e collectively or cooperatively present radial symmetry about the bracket 238 and, in turn, the rod 214 (i.e., at one hundred eighty degree (180°) intervals) both when the bag holder 216 is in the collapsed configuration and when the bag holder 216 is in the expanded configuration.

Most preferably, the support members 236a-e collectively extend laterally (or sideways) relative to the rod 214 when the bag holder is in the expanded configuration. Most preferably, the support members 236a-c extend horizontally (or orthogonally relative to the rord 214) when the bag holder 216 is in the expanded configuration. It is also most preferred that each individual one of the support members 236a-e extends orthogonally relative to the rod 214 (or, alternatively stated, horizontally) when the bag holder 216 is in the expanded configuration.

Figure 6:
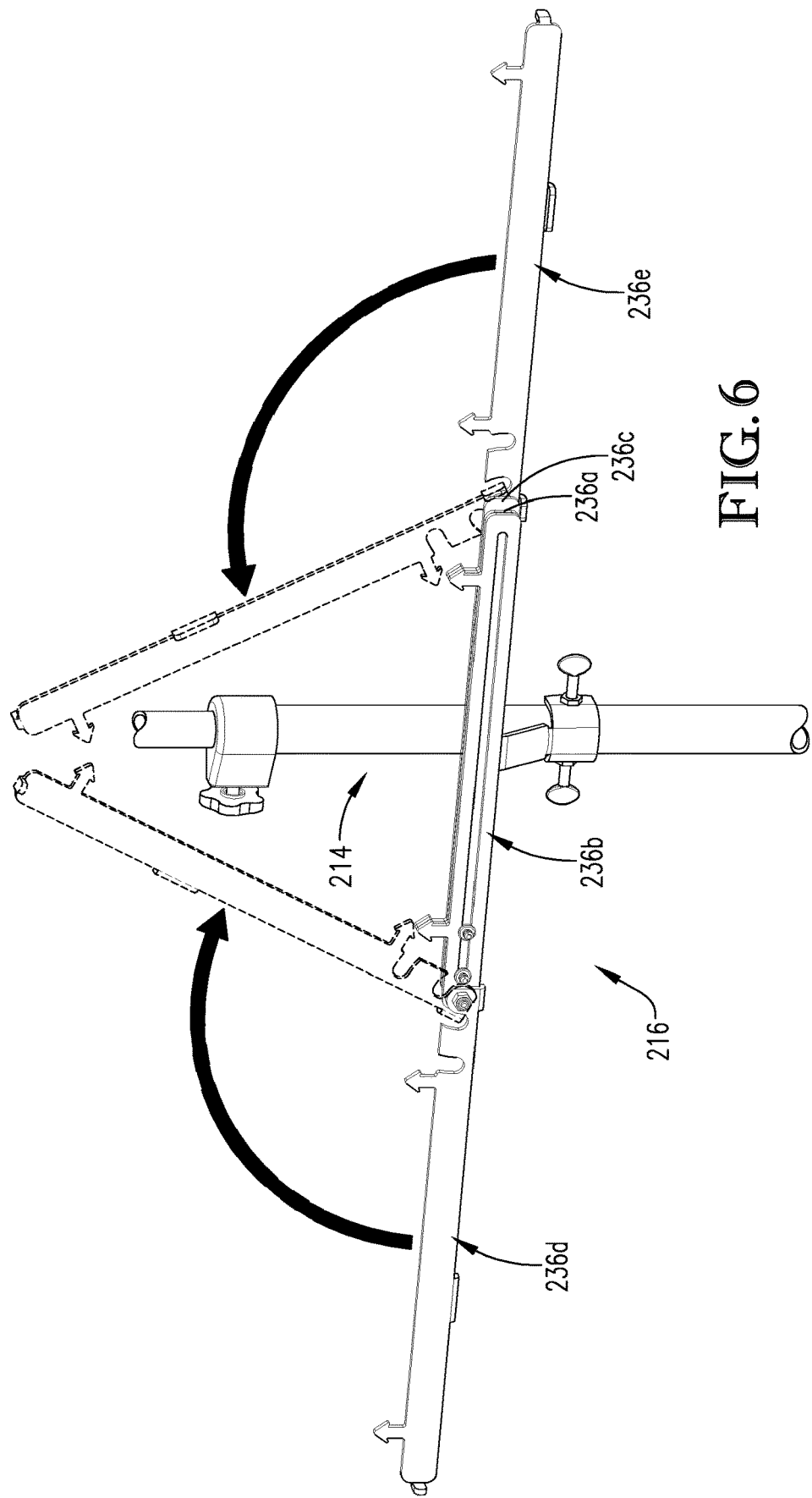
FIG. 6 is a front perspective view of the portion of the rack of FIG. 5, in an intermediate (partially closed or partially opened) configuration.
Figure 7:
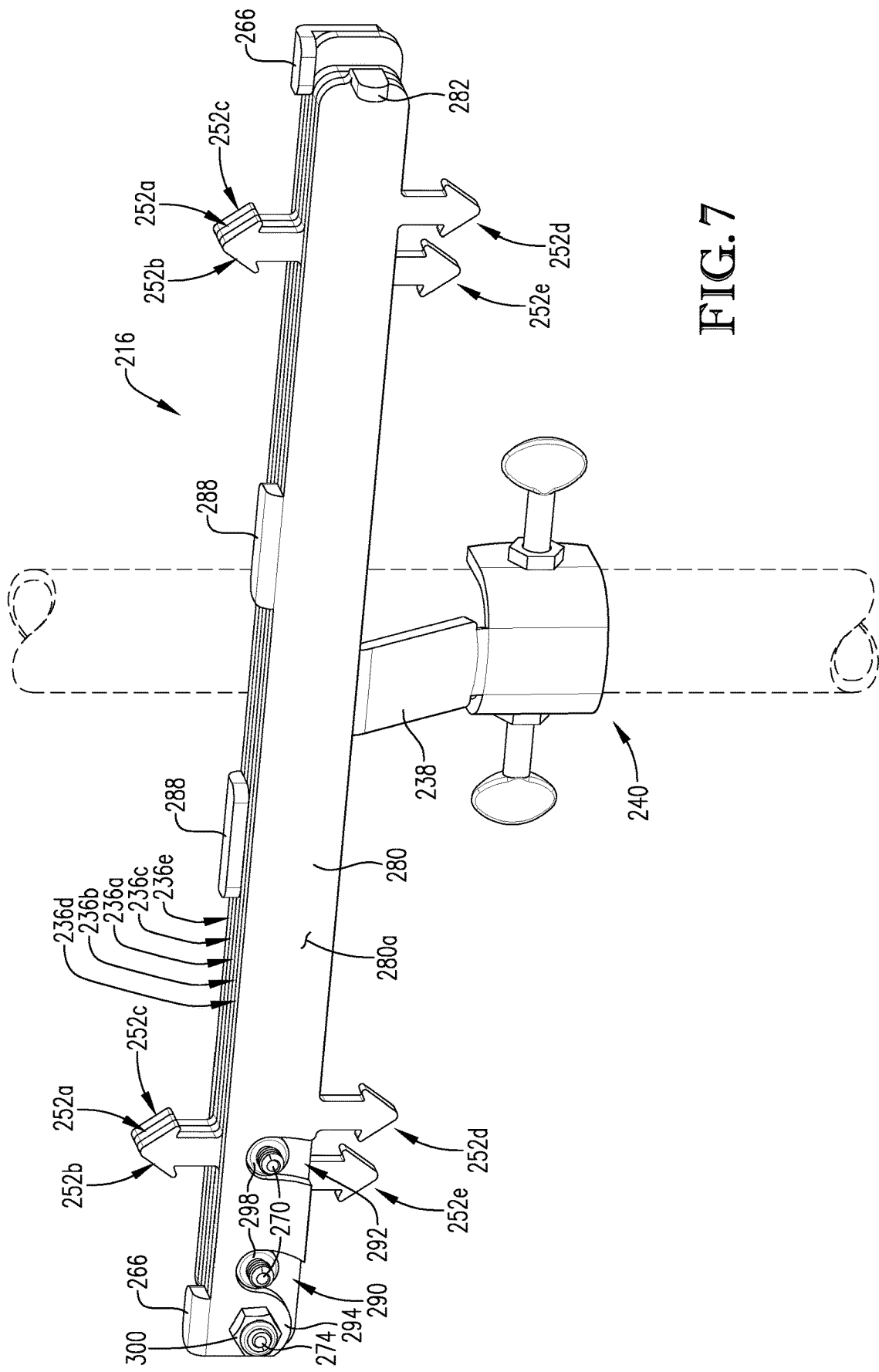
FIG. 7 is a front perspective view of the portion of the rack of FIGS. 5 and 6, in a fully contracted or closed configuration.
Figure 8:
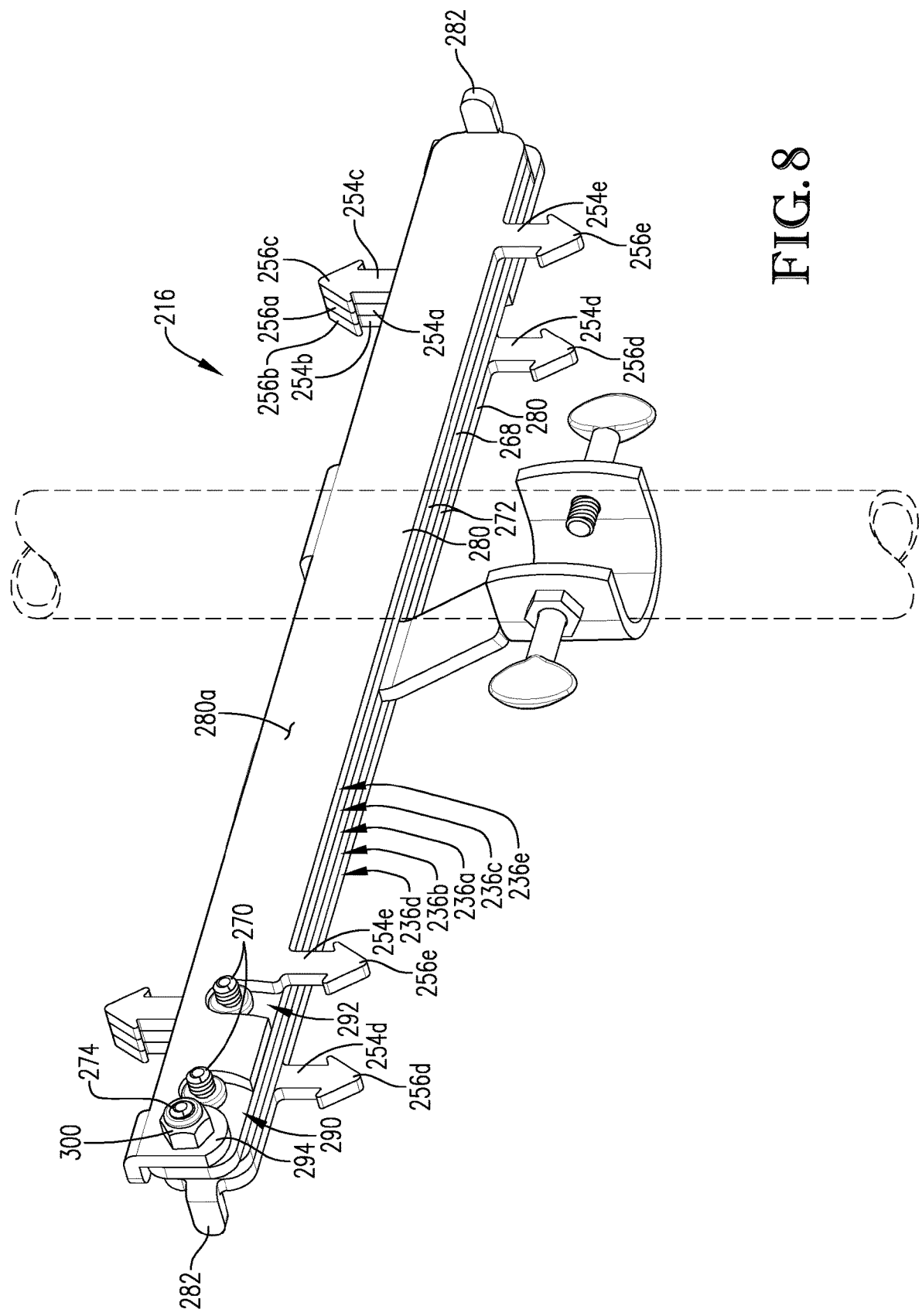
FIG. 8 is a rear perspective view of the portion of the rack of FIGS. 5-7, in a fully contracted or closed configuration.

FIGS. 5 and 6 illustrate a process of collapsing the rack 210 from a fully expanded configuration, through intermediate stages, to a compact, fully contracted configuration best shown in FIGS. 7 and 8. As shown in FIG. 5, for instance, a preferred first step in the collapsing process involves the loosening of the washers 298 and subsequent laterally inward sliding of the slidable support members 236b and 236c relative to the foundational support member 236a. Upon completion of this step, as illustrated in FIG. 6, the hooks 252a-c are fully aligned with one another.

A preferred second step in the collapsing process involves the loosening of the nuts 300 and subsequent inward pivoting of the pivotable support members 236d and 236e (in a vertical plane). As shown in FIG. 7, upon completion of this step, the projections 270 of the foundational support member 236a, along with the washers 298 threaded thereon, are received in respective ones of the notches 290 and 292. The curvature of the rounded portion 294 adjacent the notch 290 provides necessary clearance to enable such pivoting.

Although the above-described method for collapsing the rack 210 is a preferred method, various other methods may be used, including methods in which the above-described steps are simply performed in a different order.

It is also noted that expansion of the rack 210 preferably occurs simply through a reversal of the method described above for collapse of the rack 210. However, it is again permissible for alternative expansion methods to be used.

In the collapsed configuration of the rack 210, the hooks 252d and 252e extend downward, with the hooks 252d being laterally offset from the hooks 252e. One of the tabs 282 extends forward (from pivotable support member 236d), and another of the tabs 282 extends rearward (from pivotable support member 236e). The tabs provide a gripping point for (preferably manually) initiating a later expansion of the rack 210. The lips 284 and 288 extend over the tops of adjacent ones of the support members 236a-c to restrict inadvertent shifting thereof. More particularly, as shown in FIG. 7, the proximal lip 284 and intermediate lip 288 of the pivotable support member 236d extend over the sliding support member 236b and the foundational support member 236a. The proximal lip 284 and the intermediate lip 288 of the pivotable support member 236e extend over the sliding support member 236c and the foundational support member 236a.

As best shown in FIGS. 7 and 8, in the fully contracted or collapsed configuration of the rack 210, the ends 260 of the slidable support member 236b align with the ends 264 of the adjacent pivotable support member 236d. Similarly, the ends 260 of the other slidable support member 236c align with the ends 264 of the other pivotable support member 236e. However, the ends 260 and 264 of the support members 236b and 236d, respectively, are laterally offset from the corresponding ends 260 and 264 of the support members 236c and 236e, respectively. Furthermore, each end 258 of the foundational support member 236a aligns with only one pair of the ends 260 and 264. More particularly, the ends 258 align with the more proximally disposed ones of the ends 260 and 264, in keeping the shorter lateral span of the foundational support member 236a in comparison to that of each of the remaining support members 236b-e. That is, the support members 236b and 236d each extend past the support member 236a in a first direction, while the support members 236c and 236e each extend past the support member 236a in a second direction.

It is noted that the bodies 268, 272, and 280 of the support members 236a-e all extend parallel to one another in both the fully expanded and fully contracted configurations of the bag holder 216. Still further, the bodies 268, 272, and 280 move in or are positioned in parallel planes in any intermediate configurations (i.e., those between fully expanded and fully contracted configurations).

In view of the above, it will be apparent that a collective fore-and-aft depth of the support members 236a-e remains constant regardless of the degree of expansion thereof. That is, the depth of the support members 236a-e in the fully contracted configuration, the fully expanded configuration, and any intermediate configurations remains constant.

The fore-and-aft depth of the support members 236a-e is preferably between about five tenths inches (0.5") and about three inches (3"). More preferably, the fore-and-aft depth is between about one inch (1") and about two inches (2"). Most preferably, the fore-and-aft depth is about one and three hundred eighty-five thousandths inches (1.385").

It is noted that, in some embodiments, certain of the fore-and-aft extending components might be provided with collapsing capability. For instance, the tabs and/or lips in an alternative embodiment might be collapsible for even more compact storage. In such an instance, it is noteworthy that, despite potential variability in the fore-and-aft depth of the support members in a broad sense (i.e., including tabs, lips, etc.), a collective fore-and-aft depth of the bodies 268, 272, and 280 is nevertheless constant. In the illustrated embodiment, for instance, the bodies 268, 272, and 280 collectively present a constant depth of about six hundred twenty-five thousandths inches (0.625").

Furthermore, a collective lateral collapsed or contracted width or span of the all of the support members 236a-e is minimized when the rack 210 is in a fully contracted or collapsed configuration. The collapsed width is preferably between about five inches (5") and about twenty inches (20"). More preferably, the collapsed width is between about seven and five tenths inches (7.5") and about fifteen and five tenths inches (15.5"). Most preferably, the collapsed width is about eleven and five tenths inches (11.5").

Preferably, the expanded width is at least two (2) times the collapsed width. More preferably, the expanded width is at least three (3) times the collapsed width. Still more preferably, the expanded width is at least four (4) times the collapsed width. Most preferably, the expanded width is about four and five tenths (4.5) times the collapsed width.

The expandable and collapsible support rack 210 described above provides numerous advantages. Among other things, for instance, the rack 210 in its fully expanded configuration enables an advantageously high number of sponge bags 248a-e to be hung on a single side, fully visible from any one of numerous single vantage points. In turn, an unobstructed count of numerous used surgical sponges may be obtained from a single vantage point, eliminating unnecessary movement by the "counter" of the sponges to shift overlapping bags, view the rack 210 from another side, etc.

The rack 210 also requires a very small floor footprint in contrast to its significant display capacity, while also being collapsible into a very small overall envelope to take minimal space when not in use.

Still further, partial expansion or contraction of the rack 210 is feasible, enabling surgical practitioners to determine the most appropriate balance between space usage and display capacity. For instance, in a crowded operating theater associated with a surgery requiring only a moderate number of sponges, the rack 210 might be opened only to the configuration shown in FIG. 6, in which three (3) bags can be hung on three (3) support members.

It is again noted that, although five (5) support members 236a-e are illustrated, it is permissible according to some aspects of the present invention for more or fewer support members to be provided. Furthermore, the support members might be alternatively arranged (e.g., placed in a different order) or, according to some aspects of the present invention, include proportionally more or fewer slidable members or pivotable members. Exclusive use of pivoting members or of sliding members also falls within the scope of some aspects of the present invention.

Still further, variations in the configurations of individual support members may occur. For instance, certain aspects of the present invention encompass a foundational support member that is configured so that each half thereof is angled relative to or offset from (e.g., neither parallel to nor aligned with) the other half. The halves might also vary in lateral extent or in general configuration (e.g., be non-symmetrical relative to each other). It is noted that such alternative configurations would likewise result in a bag holder that is as a whole comprised of non-symmetrical, non-identical, angled, and/or offset lateral halves or portions.

In another embodiment, the bag holder might have asymmetrical sides at least with respect to the manner in which the support members are intercoupled. For instance, to maintain balance, the sides might project equidistantly relative to the foundational support member and also have similar weight (although some variance is acceptable according to some aspects of the present invention), yet be operably coupled to one another differently on one side than on the other. That is, pivotable support members might be provided on one side and slidable support members on the other, varying combinations of shiftability might be provided on each side, etc.

Design 2: Slidable J-Handle Support Members

FIGS. 15-19 illustrate a second preferred surgical sponge rack 310. It is initially noted that, with certain exceptions to be discussed in detail below, many of the elements of rack 310 of the second embodiment are the same as or very similar to those described in detail above in relation to the rack 210 of the first embodiment. Therefore, for the sake of brevity and clarity, redundant descriptions and numbering will be generally avoided here. Unless otherwise specified, the detailed descriptions of the elements presented above with respect to the first embodiment should therefore be understood to apply at least generally to the second embodiment, as well.

Similarly to the rack 210, the rack 310 of the second preferred embodiment preferably includes a base 312, a mounting rod 314, a bag holder 316, and a top 318. The bag holder 316 includes a frame 320 and plurality of support members 322a-f secured relative to the frame 320. Bags 324a-f hang from the support members 322a-f. The bag holder 316 also preferably includes a bracket 326 and a clamp 328.

The bag holder 316 is preferably formed of metal, although other materials fall within the scope of the present invention.

As illustrated, the frame 320 preferably is in the form of a rounded rectangle (i.e., a rectangle with rounded corners) including a top and bottom 320a and 320b, respectively, and sides 320c and 320d. The frame 320 is fixed to the bracket 326, which in turn is fixed to the clamp 328. The clamp 328 is secured relative to the rod 314 to support the support members 322a-f on the rod 314.

The bracket 326 preferably extends in a forward direction such that the support members 322a-f are disposed on a front side of the rack 310 (i.e., on one side of the rod 314) in a general sense.

The support members 322a-f preferably include front and rear foundational support members 322a and 322b, respectively; front and rear intermediate support members 322c and 322d, respectively; and front and rear distal or outer support members 322e and 322f, respectively. (As noted above, all of the support members 322a-f are disposed on a front side of the rack 310 in a general sense. "Front" and "rear" are used here in a more local sense to describe the positions of the support members 322a-f relative to each other. That is, the support members 322a,c,e are disposed forward of the support members 322b,d,f; but all support members 322a-f are forward of the rod 314.)

The foundational support members 322a and 322b are preferably integrally formed with one another and, more particularly, are preferably unitarily formed. As will be discussed in greater detail below, the intermediate support members 322c and 322d are preferably laterally slidable relative to respective ones of the foundational support members 322a and 322b, while the outer support members 322e and 322f are laterally slidable relative to respective ones of the intermediate support members 322c and 322d.

Preferably, each support member 322a-f includes a pair of pegs or hooks 330a-f projecting upwardly therefrom when the support members 322a-f (or, alternatively stated, the rack 310 or the bag holder 316) are in an expanded configuration. Each hook 330a-f preferably includes a respective base 332a-f and a head 334a-f, with each head 334a-f restricting slippage of a corresponding mounted bag 324a-f off of the corresponding support member 322a-f.

In the illustrated embodiment, the bases 332a-f are preferably in the form of cylindrical posts. The heads 334a-f are preferably in the form of radially enlarged cylinders or disks. A variety of hook shapes fall within the scope of the present invention, however.

The support members 322a-f are each preferably generally J-shaped, with a straight, longitudinally (i.e., laterally) extending arm 338a-f and a curved handle 340a-f. Each arm 338a-f presents proximal and distal (i.e., inner and outer) ends 342a-f and 344a-f, respectively. Each handle 340a-f extends from the corresponding one of the outer ends 344a-f.

The arms 338a-f and handles 340a-f of each of the support members 322a-f are preferably structural identical to one another, although variations are permissible within the scope of the present invention.

In the illustrated embodiment, the arms 338a-f are generally hexagonally prismatic in form, although other shapes (e.g., circularly cylindrical, rectangularly prismatic, etc.) are permissible.

The arm 338a of the front foundational support member 322a is disposed forward of the arm 338b of the rear foundational support member 322b. Furthermore, a portion of the front arm 338a laterally overlaps (but preferably is not in direct contact with) a portion of the rear arm 338b, such that an overlapping region 346 is cooperatively defined by the arms 338a and 338b.

The handle 340a of the front foundational support member 322a curves or extends backward. The handle 340b of the rear foundational support member 322b curves or extends forward. Most preferably, the extension of the handles 340a and 340b is such that an end 348 of the handle 340a of the front foundational support member 322a is at least in part laterally aligned with the arm 338b of the rear foundational support member 330b. Similarly, an end 350 the handle 340b of the rear foundational support member 322b is most preferably at least in part laterally aligned with the arm 338a of the front foundational support member 322a. Disalignment is permissible without departing from the scope of the present invention, however.

Preferably, the front and rear foundational support members 322a and 322b are identical to each other. That is, they vary only in orientation (and not in structure). Numerous variations fall within the scope of the present invention, however.

In keeping with the above-described preferred alignment of handle ends 348 and 350 with arms 348b and 248a, respectively, it is noted that the overlapping portions of the front and rear foundational support members 322a and 322b that define the aforementioned overlapping region 346 most preferably do not include the entirety of the respective arms 348a and 348b. Furthermore, in view of their preferred structural conformity, it will be apparent that the hooks 330a of the front foundational support member 322a are laterally offset from the hooks 330b of the rear foundational support member 330b in a preferred embodiment of the rack 210. As will be discussed in greater detail below, the offset nature of the hooks 330a and 330b ensures that bags 324a and 324b hanging therefrom will not overlap in their entirety, although partial overlap occurs the illustrated preferred embodiment.

In contrast to the foundational support members 322a,b, each intermediate support member 322c,d and outer support member 322e,f preferably includes a sleeve 352c-f extending forward or rearward from the corresponding arm 338c-f.

More particularly, the sleeves 352c-f and 352e of the front intermediate and outer support members 322c and 322e, respectively, preferably include a respective bottom portion 354c,e extending rearwardly from a bottom surface 356c,e of each respective arm 338c,e. Furthermore, a pair of side portions 358c,e extends upwardly from the respective bottom surface 356c,e. Each pair of side portions 358c,e defines a respective channel 360c,e therebetween.

The side portions 358c of the sleeve 352c of the front intermediate support member 322c preferably extend around the arm 338a of the front foundational support member 322a. Alternatively stated, the arm 338a of the front foundational support member 322a preferably extends through the channel 360c. The side portions 358e of the sleeve 352e of the front outer support member 322e preferably extend around the arm 338c of the front intermediate support member. Alternatively stated, the arm 338c of the front intermediate support member 322c preferably extends through the channel 360e.

In contrast, the sleeves 352d and 352f of the rear intermediate and outer support members 322d and 322f, respectively, preferably include a bottom portion 354d,f extending forwardly from a bottom surface 356d,f of each respective arm 338d,f. Furthermore, a pair of side portions 358d,f preferably extends upwardly from the respective bottom surface 356d,f. Each pair of side portions 358d,f defines a respective channel 360d,f therebetween.

The side portions 358d of the sleeve 252d of the rear intermediate support member 322d preferably extend around the arm 338b of the front foundational support member 322b. Alternatively stated, the arm 338b of the rear foundational support member 322b preferably extends through the channel 360d. The side portions 358f of the sleeve 252f of the rear outer support member 322f preferably extend around the arm 338d of the rear intermediate support member 322d. Alternatively stated, the arm 338d of the rear intermediate support member 322d preferably extends through the channel 360f.

Thus, the front outer support member 322e is longitudinally slidable along the arm 338c of the front intermediate support member 322c, which in turn is longitudinally slidable along the arm 338a of the front foundational support member 322a. Similarly, the rear outer support member 322f is longitudinally slidable along the arm 338d of the rear intermediate support member 322d, which in turn is longitudinally slidable along the arm 338b of the rear foundational support member 322b.

In the illustrated embodiment, the channels 360c-f are each generally hexagonally prismatic in form, although other shapes (e.g., circularly cylindrical, rectangularly prismatic, etc.) are permissible. Most preferably, pairs of channels and arms are shaped to correspond to one another to facilitate efficient sliding of the arms within the respective channels.

As will be discussed in greater detail below, the slidability of the various support members 322a-f of the rack 310 of the second preferred embodiment enables expansion and contraction of the rack 310 in a manner similar to the rack 210 of the first preferred embodiment and confers similar advantages.

Each of the foundational support members 322a and 322b and intermediate support members 322c and 322d preferably includes a stopper peg 362a-d extending forward or rearward therefrom. More particularly, the front foundational and intermediate support members 322a and 322c include respective pegs 362a and 362c extending rearward therefrom. The rear foundational and intermediate support members 322b and 322d include respective pegs 362b and 362d extending forward therefrom. The pegs 362a-d preferably extend from respective ones of the outer ends 344a-d of the arms 338a-d, so as to be disposed at the juncture of each respective set of arms 338a-d and handles 340a-f.

Presence of additional stopper pegs is permissible without departing from the scope of the present invention, as is alternative positioning of the stopper pegs. Most preferably, however, any stopper pegs that are provided will serve functional roles at least similar to those described below with regard to the illustrated pegs 362a-d.

Figure 15:
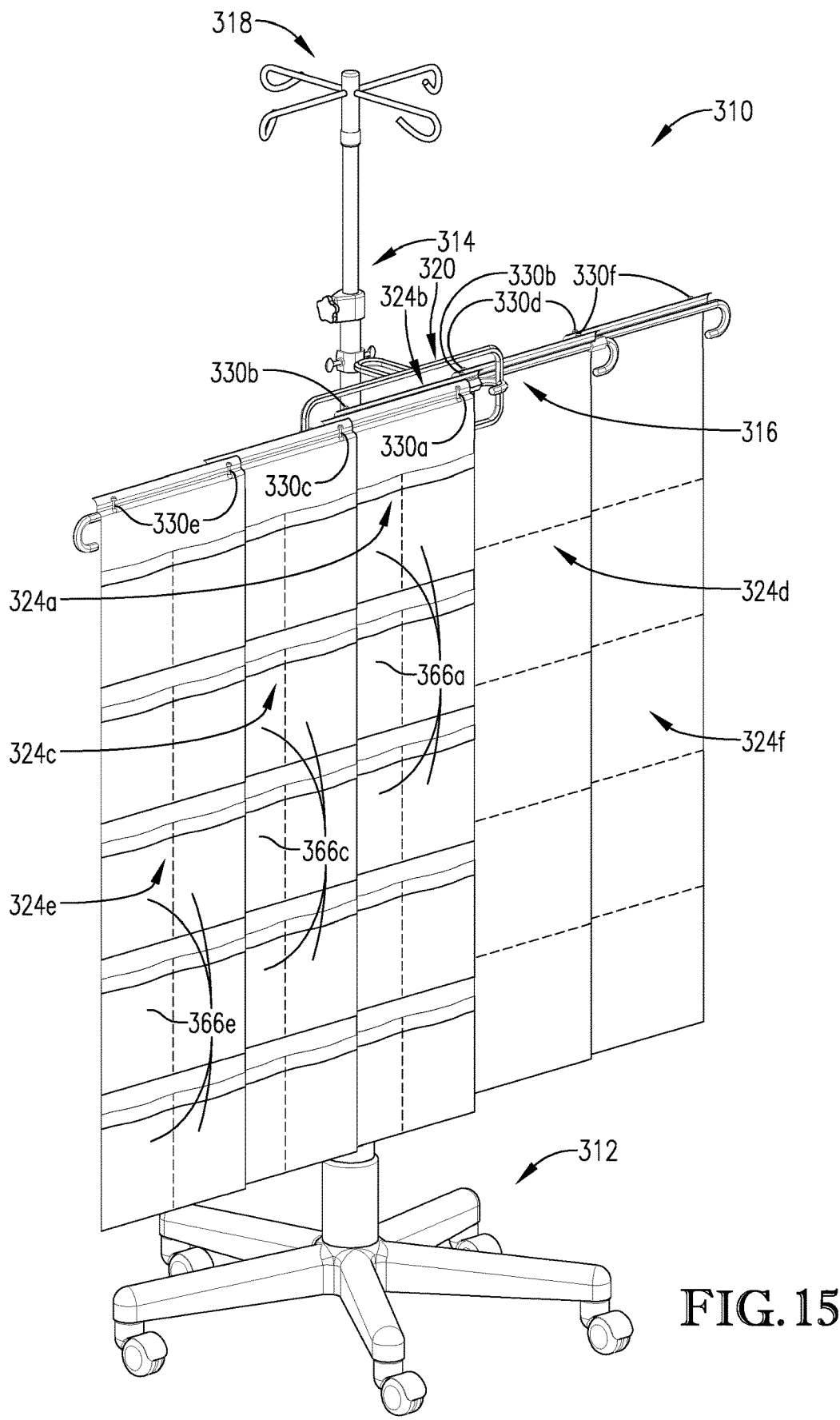
FIG. 15 is a front perspective view of a surgical sponge inventory rack according to a second preferred embodiment of the present invention, particularly illustrating a fully open or expanded configuration.
Figure 16:
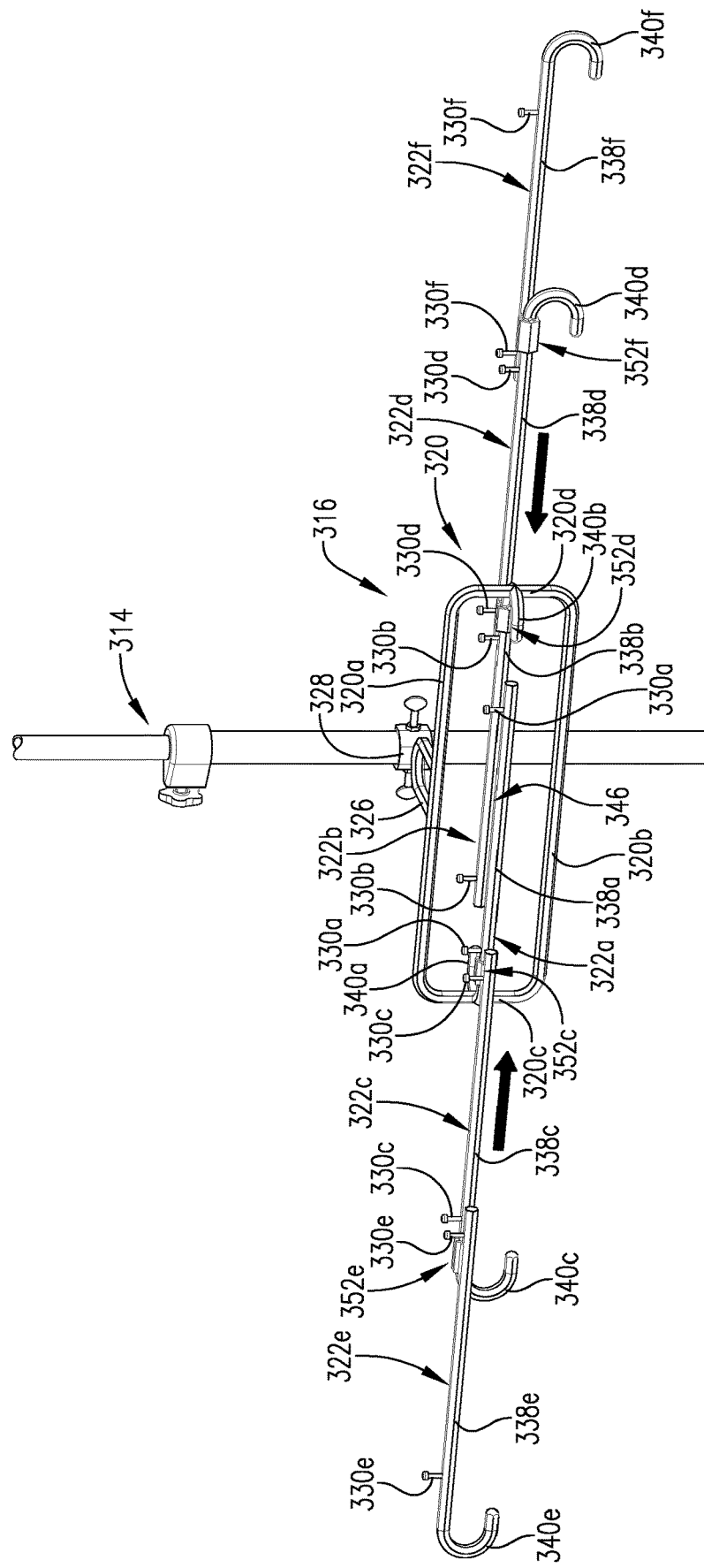
FIG. 16 is an enlarged front perspective view of a portion of the rack of FIG. 15, in a fully open or expanded configuration.

As shown in FIGS. 15 and 16, in a fully expanded state, the intermediate support members 322c and 322d are positioned laterally outward relative to the foundational support members 322a and 322b. Similarly, the outer support members 322e and 322f and are disposed laterally outward of the intermediate support members 322c and 322d. The extent to which the support members 322a-f and are laterally offset from one another is dictated by the stopper pegs 362a-d and the sleeves 352c-f.

More particularly, further outward shifting of the front outer support member 322e is prevented by engagement of an outer face of its sleeve 352e with the peg 362c of the front intermediate support member 322c. Further outward shifting of the front intermediate support member 322c is prevented by engagement of an outer face of its sleeve 362c with the peg 362a of the front foundational support member 322a.

Likewise, further outward shifting of the rear outer support member 322f is prevented by engagement of an outer face of its sleeve 352f with the peg 362d of the rear intermediate support member 322d. Further outward shifting of the rear intermediate support member 322d is prevented by engagement of an outer face of its sleeve 362d with the peg 362b of the rear foundational support member 322b.

As illustrated, a collective lateral expanded width or span of the all of the support members 322a-f is at least substantially maximized when the rack 310 is in a fully expanded configuration. The expanded width is preferably between about thirty inches (30") and about seventy inches (70"). More preferably, the expanded width is between about forty inches (40") and about sixty inches (60") inches. Most preferably, the expanded width is about forty-nine and ten hundredths inches (49.10").

Furthermore, it will be apparent that the support members 322a-f are collectively (i.e., when viewed as a whole) centered relative to the rod 314. Still further, the support members 322a-f collectively or cooperatively present radial symmetry about the rod 314 (i.e., at one hundred eighty degree (180°) intervals).

Preferably, interaction of certain ones of the sleeves 352c-f with certain ones of the hooks 330a-f provides further control of the sliding or shifting process of the support members 322c-f. Such control might restrict, among other things, rotation of the support members relative to one another along a longitudinal or lateral axis. For instance, during shifting of the front outer support member 322e relative to the front intermediate support member 322c, the sleeve 352e preferably passes by the outer one of the hooks 330c. Alternatively stated, the base 332c of the hook 330c passes through a gap 364e defined between the ends of the side portions 358e of the sleeve 352e, above the channel 360e. During shifting of the front intermediate support member 322c relative to the front foundational support member 322a, the sleeve 352c preferably passes by the outer one of the hooks 330a. Alternatively stated, the base 332a of the hook 330a passes through a gap 364c defined between the ends of the side portions 358c of the sleeve 358c, above the channel 360c.

During shifting of the rear outer support member 322f relative to the rear intermediate support member 322d, the sleeve 352f preferably passes by the outer one of the hooks 330d. Alternatively stated, the base 332d of the hook 330d passes through a gap 364f defined between the ends of the side portions 358f of the sleeve 358f, above the channel 360f During shifting of the rear intermediate support member 322d relative to the rear foundational support member 322b, the sleeve 352d preferably passes by the outer one of the hooks 330b. Alternatively stated, the base 332b of the hook 330b passes through a gap 364d defined between the ends of the side portions 358d of the sleeve 358d, above the channel 360d.

It is noted that is permissible according to some aspects of the present invention for additional projections to also be provided to further guide the relative motion of the support members. For instance, a continuous rib and/or one or more discrete projections might be provided.

Furthermore, rotational restriction of the support members 322c-f about the respective longitudinal axes of the arms 338c-f thereof may be provided simply by the geometries of the arms 338c-f relative to the sleeves 352c-f and the channels 360c-f. For instance, whereas circularly cylindrical arms in correspondingly shaped channels would rotate at least substantially freely within their corresponding sleeves (absent other constraints), hexagonally prismatic arms 338c-f such as those illustrated are restricted from rotating in the channels 360c-f at least in part due to the fitted nature of the sleeves 352c-f, the congruent shape of the channels 360c-f, and the presence of flat sides and corners associated with the hexagonal cross-sectional shape.

As illustrated in FIG. 15, three (3) bags 324a,c,e, each including ten (10) pockets 366a,c,e, are preferably substantially visible from a front vantage point (when hanging from respective ones of the front support members 322a,c,e). Although the bags 366a and 366c and the bags 366c and 366e overlap slightly, any sponges that might be contained in the pockets 366a,c,e would remain visible and easily accounted for. An additional two (2) bags (not illustrated for purposes of clarity), each also including ten (10) pockets, preferably hang from the rear support members 322d,f in such a manner that the pockets thereof face forward. These additional bags may also overlap slightly with one another and with bag 366a in the manner described above; however, any sponges contained therein should likewise remain substantially visible and easily accounted for. It is noted that "substantially" as used in the present sense should be understood to mean simply that any overlap that occurs between adjacent bags is small enough that any sponges held in said bags are readily visible for easy and unambiguous counting.

Similarly, as illustrated in FIG. 15, three (3) bags 324b,d,f, each including ten (10) pockets 366b,d,f, are preferably substantially visible from a rear vantage point (when hanging from respective ones of the rear support members 322b,d,f). Although the bags 366b and 366d and the bags 366d and 366f overlap slightly, any sponges that might be contained in the pockets 366b,d,f would remain visible and easily accounted for. An additional two (2) bags (not illustrated for purposes of clarity), each also including ten (10) pockets, preferably hang from the front support members 322c,e in such a manner that the pockets thereof face rearward. These additional bags may also overlap slightly with one another and with bag 366b in the manner described above; however, any sponges contained therein should likewise remain substantially visible and easily accounted for. It is noted that "substantially" as used in the present sense should be understood to mean simply that any overlap that occurs between adjacent bags is small enough that any sponges held in said bags are readily visible for easy and unambiguous counting.

Thus, as many as fifty (50) sponges could be visually accounted for from a single vantage point, with as many as one hundred (100) sponges visible in total (from two (2) vantage points) without any shifting of bags being necessary.

As shown in FIG. 16, in a preferred method of collapsing the rack 310, the intermediate support members 322c and 322d are first slid laterally inwardly along respective ones of the arms 338a and 338b of the foundational support members 322a and 322b. The outer ones of hooks 330a and 330b pass through corresponding gaps 364c and 364d in sleeves 352c and 352d. Engagement of pegs 362c and 362d with respective ones of the sleeves 352e and 352f forces the outer support members 322e and 322f to also shift inward along with the intermediate support members 322c and 322d. Inward shifting of the intermediate support members 322c and 322d is completed upon engagement of the pegs 362c and 362d with respective sides 320c and 320d of the frame 320 (see, for instance, FIG. 17).

Figure 17:
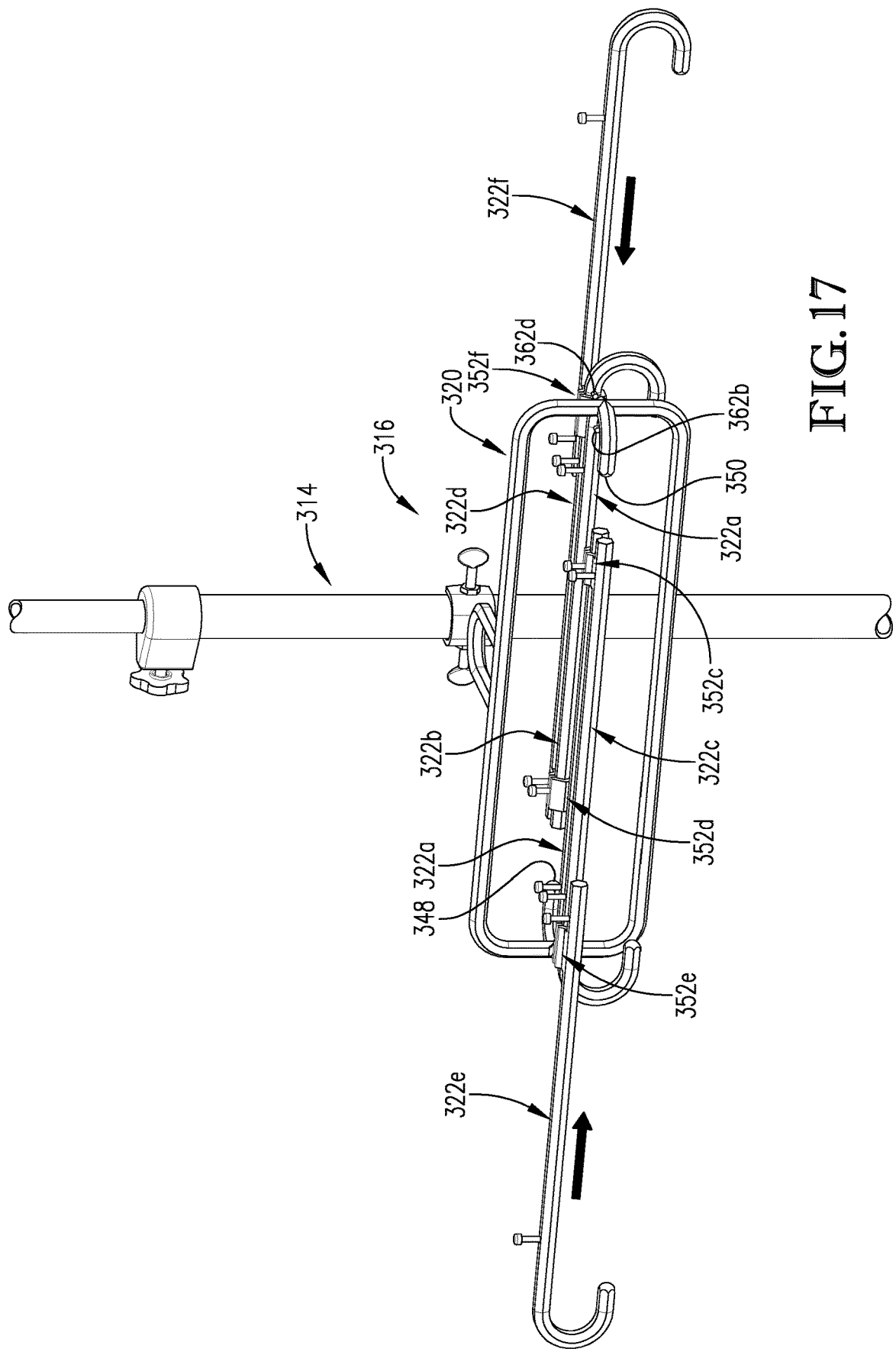
FIG. 17 is a front perspective view of the portion of the rack of FIG. 16, in an intermediate (partially closed or partially opened) configuration.
Figure 18:
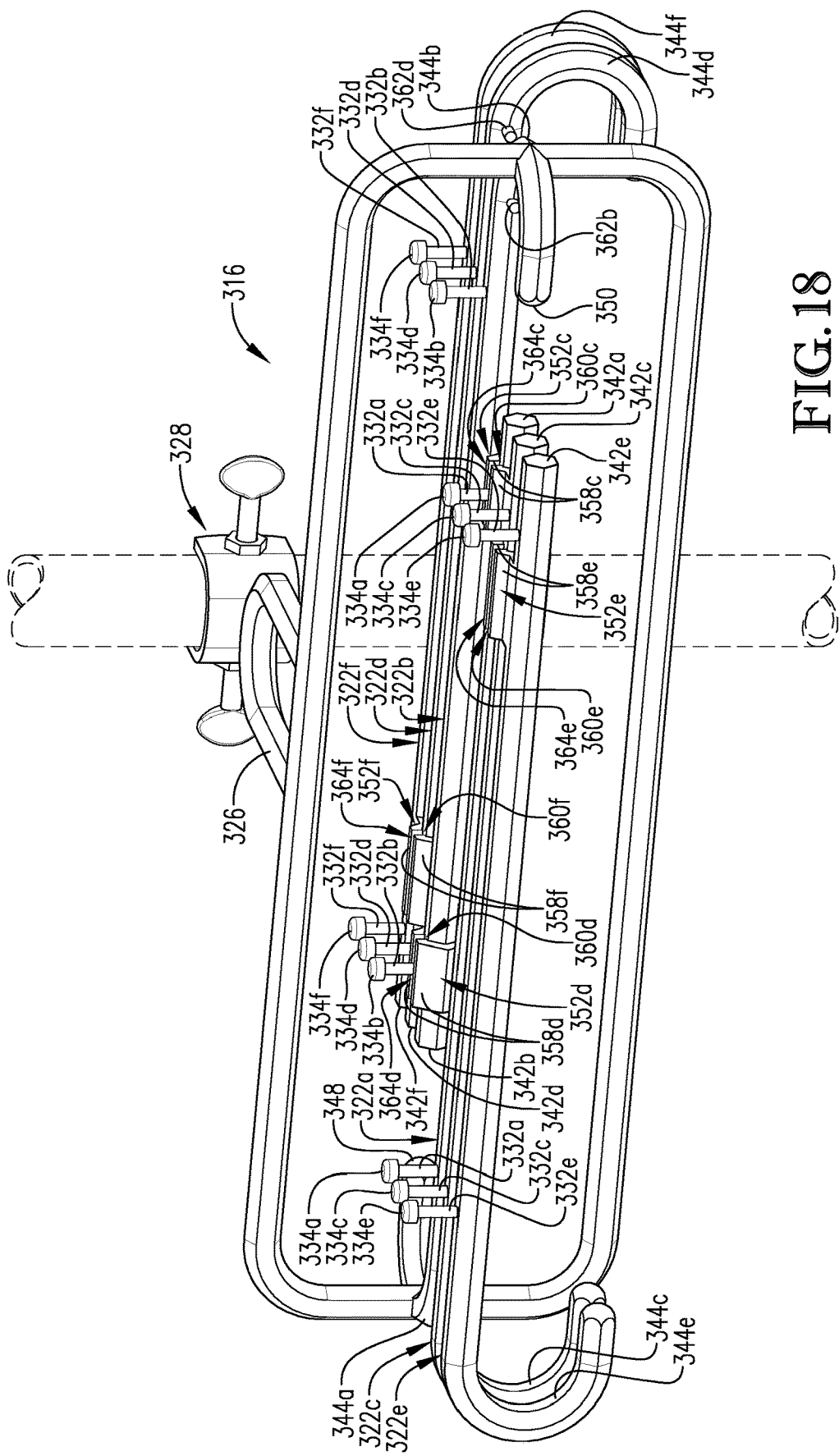
FIG. 18 is a front perspective view of the portion of the rack of FIGS. 16 and 17, in a fully contracted or closed configuration.
Figure 19:
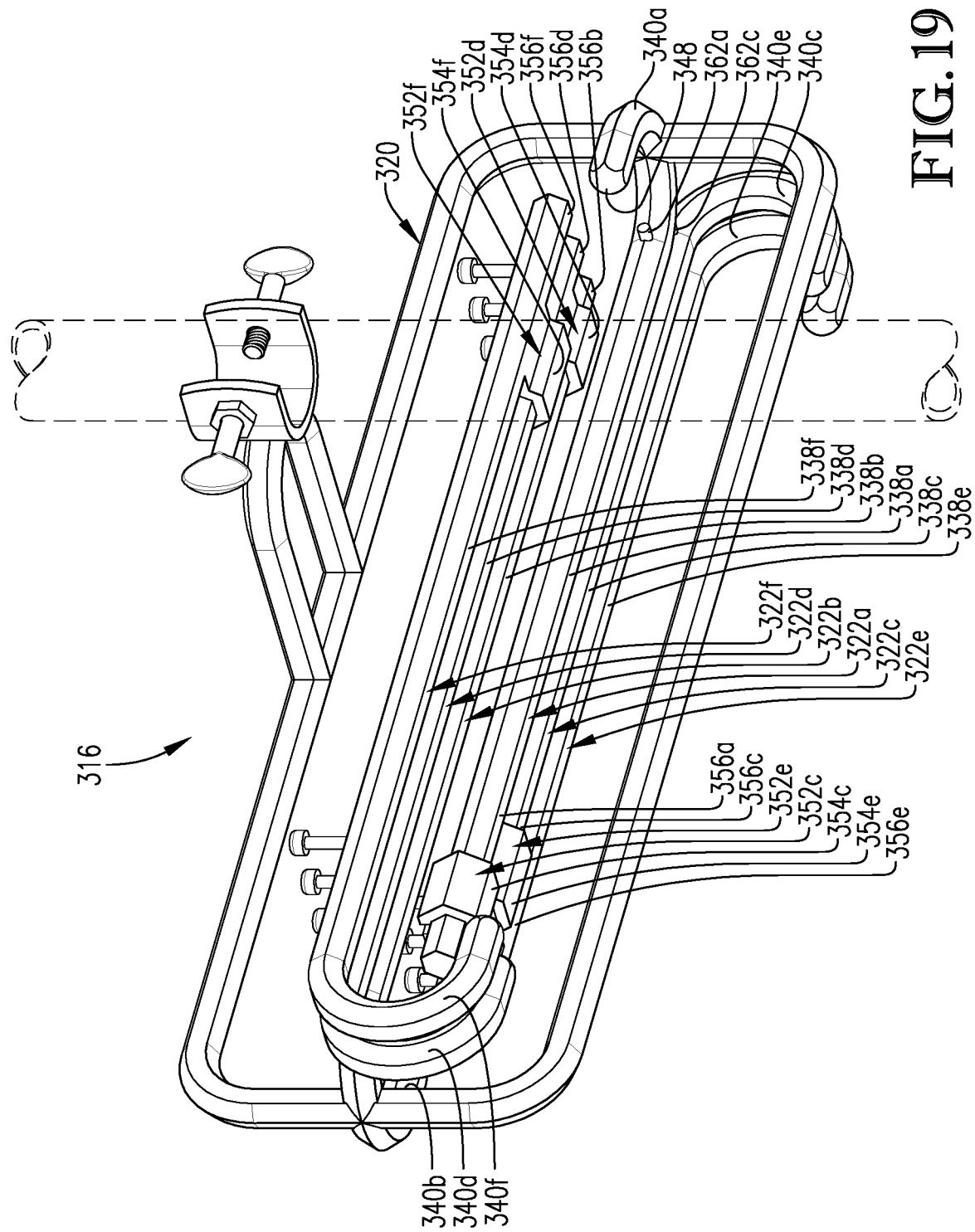
FIG. 19 is a rear perspective view of the portion of the rack of FIGS. 16-18, in a fully contracted or closed configuration.

As shown in FIG. 17, the outer support members 322e and 322f are then preferably slid laterally inwardly along respective ones of the arms 338c and 338d of the intermediate support members 322c and 322d. The outer ones of hooks 330c and 330d pass through corresponding gaps 364e and 364f in sleeves 352e and 352f. Inward shifting of the outer support members 322e and 322f is completed upon engagement of the sleeves 352e and 352f thereof with corresponding ones of the sleeves 352c and 352d of the intermediate support members 322c and 352d. The fully closed or compact configuration is illustrated in FIGS. 18 and 19.

Although the above-described method for collapsing the rack 310 is a preferred method, various other methods may be used, including but not limited to methods in which the above-described steps are simply performed in a different order.

It is also noted that expansion of the rack 310 preferably occurs simply through a reversal of the method described above for collapse of the rack 310. However, it is again permissible for alternative expansion methods to be used.

A collective lateral collapsed or contracted width or span of all of the support members 322a-f is preferably minimized when the rack 310 is in a fully contracted or collapsed configuration. The collapsed width is preferably between about five inches (5") and about twenty-five inches (25"). More preferably, the collapsed width is between about ten inches (10") and about twenty inches (20"). Most preferably, the collapsed width is about fifteen and one tenth inches (15.1").

Preferably, the expanded width is at least two (2) times the collapsed width. More preferably, the expanded width is at least three (3) times the collapsed width. Most preferably, the expanded width is about three and twenty-five hundredths (3.25) times the collapsed width.

It is also noted that the arms 338a-f of the support members 322a-f all extend parallel to one another in both the fully expanded and fully contracted configurations of the bag holder 316, as well as during any movements that occur during expansionary or contractionary processes.

In view of the above, it will be apparent that a collective fore-and-aft depth of the support members 338a-f remains constant regardless of the degree of expansion thereof. That is, the depth of the support members 338a-f in the fully contracted configuration, the fully expanded configuration, and any intermediate configurations remains constant.

The fore-and-aft depth of the support members 338a-f is preferably between about two inches (2") and about six inches (6"). More preferably, the fore-and-aft depth is between about three inches (3") and about five inches (5"). Most preferably, the fore-and-aft depth is about four and one tenth inches (4.1").

It is further noted that the collective vertical height of the support members 338a-f (including the hooks 330a-f) also remains constant regardless of the degree of expansion thereof. That is, the vertical height of the support members 338a-f in the fully contracted configuration, the fully expanded configuration, and any intermediate configurations remains constant. Most preferably, the height is between about one inch (1") and about four inches (4"). More preferably, the height is between about two inches (2") inches and about three inches (3"). Most preferably, the height is about two and four tenths inches (2.4").

It is noted that the collective vertical height of the arms 338a-f and handles 340a-f of the support members 338a-f (i.e., excluding the hooks 330a-f) is likewise preferably constant regardless of the degree of expansion thereof. That is, the vertical height of the arms 338a-f and handles 340a-f of the support members 338a-f in the fully contracted configuration, the fully expanded configuration, and any intermediate configurations remains constant. Most preferably, the height is between about one and five tenths inches (1.5") and about three and five tenths inches (3.5"). More preferably, the height is between about two and five tenths inches (2.5") and about three and five tenths inches (3.5"). Most preferably, the height is about one and eighty-five hundredths inches (1.85").

Similarly to the rack 210 of the first preferred embodiment, the expandable and collapsible rack 310 described above provides numerous advantages. Among other things, for instance, the rack 310 in its fully expanded configuration enables an advantageously high number of sponge bags to be hung on a single side, fully visible from any one of numerous single vantage point. In turn, an unobstructed count of numerous used surgical sponges may be obtained from a single vantage point, eliminating unnecessary movement by the "counter" to shift overlapping bags, view the rack 310 from another side, etc. A still higher count can be obtained through use of only two (2) vantages points, such as a centered front vantage point and a centered rear vantage point, or, perhaps more conveniently, a pair of very closely spaced vantage points offset only slightly from the side of the rack 310 so as to be slightly forward and slightly aft thereof.

The rack 310 also requires a very small floor footprint in contrast to its significant display capacity, while also being collapsible into a very small overall envelope to take minimal space when not in use.

Still further, partial expansion or contraction of the rack 310 is feasible, enabling surgical practitioners to determine the most appropriate balance between space usage and display capacity. For instance, in a crowded operating theater associated with a surgery requiring only a moderate number of sponges, the rack 310 might be opened only to the configuration shown in FIG. 17, in which four (4) bags can be hung on four (4) support members in a two (2)-on-each-side configuration.

It is noted that, although six (6) support members 322a-f are illustrated, it is permissible according to some aspects of the present invention for more or fewer support members to be provided. Furthermore, the support members might be alternatively arranged (e.g., placed in a different order) or, according to some aspects of the present invention, include alternatively shiftable (e.g., pivotable) members.

Design 3: Slidable Flat Plate Support Members

FIGS. 20-29 illustrate a third preferred surgical sponge rack 410. It is initially noted that, with certain exceptions to be discussed in detail below, many of the elements of the rack 410 of the third embodiment are the same as or very similar to those described in detail above in relation to the rack 210 of the first embodiment and/or the rack 310 of the second embodiment. Therefore, for the sake of brevity and clarity, redundant descriptions and numbering will be generally avoided here. Unless otherwise specified, the detailed descriptions of the elements presented above with respect to the first and/or second embodiments should therefore be understood to apply at least generally to the third embodiment, as well.

Similarly to the racks 210 and 310, the rack 410 of the second preferred embodiment preferably includes a base 412, a mounting rod 414 extending at least substantially vertically from the base 412, a bag holder 416, and a top 418.

Similarly to the bag holders 216 and 316, and as will be discussed in greater detail below, the bag holder 416 is shiftable between fully contracted and fully expanded configurations corresponding to so-called fully contracted and fully expanded configurations of the rack 410 as a whole.

The bag holder 416 preferably includes a plurality of support members 420, 422, and 424. The bag holder 416 further preferably includes a bracket 426 supporting the support members 420, 422, and 424, and a clamp 428 supporting the bracket 426 on the rod 414. The bracket 426 preferably extends forward from the rod 414 such that the support members 420, 422, and 424 are disposed on a front side of the rack 410.

In a preferred embodiment, a plurality of bags 430a-e, each including respective pluralities of pockets 432a-e, hang from respective ones of the support members 420, 422, and 424. Most preferably, each of the bags 430a-e hangs from a front side of the rack 410 such that the pockets 432a-e are all visible from a single position, such as a vantage point in front of the rack 410.

It is noted that, in accordance with some aspects of the present invention, the bags might alternatively be hung to optimize or enable viewing from other vantage points, including but not limited to a vantage points on the side or to the rear of the rack. In the latter case, for instance, the bags might be hung on the back side of the rack. Still further, the bags might be hung in such a manner as to optimize or enable the use of multiple vantage points. For instance, a portion of the bags might be hung from a front side of the rack to facilitate viewing from a front vantage point, while another portion of the bags might be hung from a rear side of the rack to facilitate viewing from a rear vantage point.

The support members 420, 422, and 424 most preferably include a foundational support member 420, a pair of slidable intermediate support members 422, and a pair of slidable outer support members 424. It is noted that, in contrast, the outer support members 236d,e of the rack 210 of the first preferred embodiment were pivotable rather than slidable.

The foundational support member 420 is preferably centered on the rod 414 so as to extend laterally therefrom, equidistantly in two (2) opposing directions. The foundational support member 420 as a whole also preferably possesses radial (i.e. rotational) symmetry about a vertical axis defined by the rod 414.

More particularly, as best shown in FIGS. 24 and 25, the foundational support member 420 preferably includes a body 420a including opposite longitudinal ends 420b and opposite top and bottom edges 420c and 420d. The body 420a is preferably in the form of a flat plate presenting front and rear faces 420e and 420f.

A respective hook 420g is disposed inward of and adjacent each end 420b, projecting upwardly from the top edge 420c of the body 420a, such that the foundational support member 420 includes two (2) hooks 420g.

A first pair of laterally spaced apart threaded projections 420h extends rearward from the rear face 420f adjacent a first one of the ends 420b. A second pair of laterally spaced apart threaded projections 420h extends forward from the front face 420e adjacent the other of the ends 420b. An inner one of the projections 420h of each pair preferably aligns vertically with a corresponding one of the hooks 420g. That is, each hook 420g is preferably disposed directly above a corresponding one of the projections 420h.

As will be discussed in greater detail below, the projections 420h preferably extend from a lower portion of the body 420a (i.e., nearer the bottom edge 420d than the top edge 420e).

As best shown in FIGS. 26 and 27, the intermediate support members 422 are preferably identical to each other and mirror each other about the aforementioned axis. Certain variations fall within the scope of some aspects of the present invention, however.

Each intermediate support member 422 preferably includes a body 422a. The body 422a is preferably in the form of a flat plate presenting front and rear faces 422b and 422c. The body 422a preferably includes opposite proximal (inner) and distal (outer) longitudinal ends 422d and 422e. The body 422a further preferably includes and opposite top and bottom edges 422f and 422g.

The proximal ends 422d each preferably overlap or are disposed inward of the corresponding end 420b of the foundational support member 420 when the rack 410 is the expanded configuration. Respective inner overlapping regions 434 (see FIG. 21) are thus defined by the foundational support member 420 and each of the two (2) intermediate support members 422 when in intermediate and expanded configurations. (As will be apparent to those of ordinary skill in the art, the size of such overlapping regions 434 varies depending on the degree of expansion.)

Figure 22:
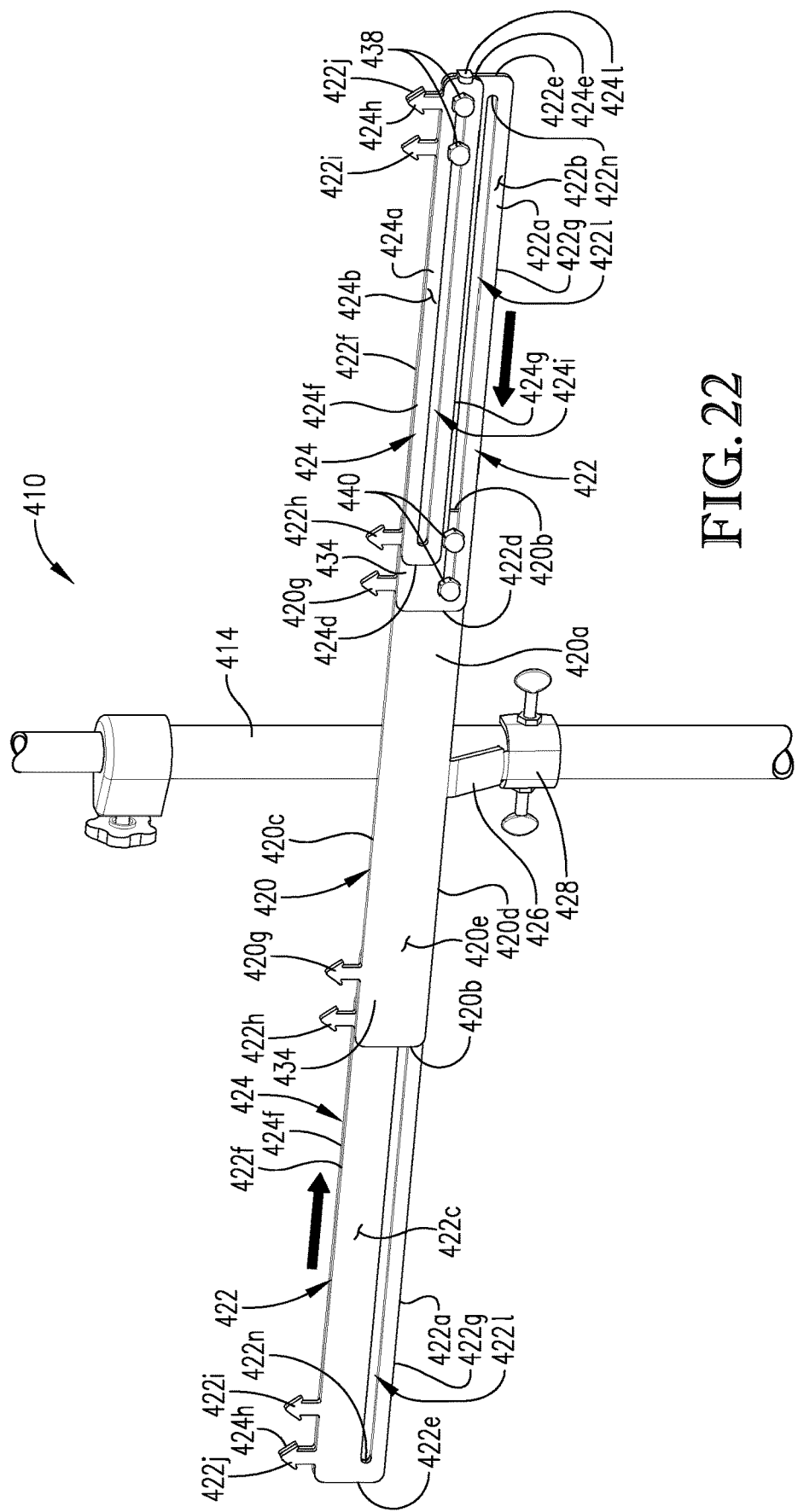
FIG. 22 is a front perspective view of the portion of the rack of FIG. 21, in an intermediate (partially closed or partially opened) configuration.

As shown in FIG. 22, each of the intermediate support members 422 preferably presents a first, proximal hook 422h disposed outward of and adjacent the inner end 422d so as to be outwardly adjacent the corresponding hook 420g of the foundational support member 420 when the rack 410 is in the expanded configuration. Each of the intermediate slidable support members 422 further preferably presents paired second and third distal hooks 422i and 422j disposed inward of and adjacent the outer end 422e.

Each intermediate support member 422 further preferably includes a pair of laterally spaced apart threaded projections 422k extending forward from the front face 422b adjacent the outer end 422e. The projections 422k preferably extend from an upper portion of the body 422a (i.e., nearer the top edge 422f than the bottom edge 422g). Each projection 422k preferably aligns vertically with a corresponding one of the distal hooks 422i and 422j That is, each hook 422i and 422j is preferably disposed directly above a corresponding one of the projections 422k.

Still further, a longitudinally extending slot 422l is preferably defined through the body 422a of each intermediate support member 422. Each slot 422l presents a pair of proximal and distal ends 422m and 422n, respectively. Each slot 422l defines a longitudinal slot length and a vertical slot height. The slot length most preferably approaches a total length of the intermediate support member 422. Each slot 422l is preferably disposed in a lower portion of the body 422a (i.e., nearer the bottom edge 422g than the top edge 422f).

As best shown in FIGS. 28 and 29, the outer support members 424 are preferably identical to each other and mirror each other about the aforementioned axis. Certain variations fall within the scope of some aspects of the present invention, however.

Each outer support member 424 preferably includes a body 424a. The body 424a is preferably in the form of a flat plate presenting front and rear faces 424b and 424c. The body 424a preferably includes opposite proximal (inner) and distal (outer) longitudinal ends 424d and 424e and opposite top and bottom edges 424f and 424g.

The proximal ends 424d each preferably overlap or are disposed inward of the corresponding distal ends 422e of the corresponding intermediate support member 422 when the rack 410 is the expanded configuration. An outer overlapping region 436 (see FIG. 21) is thus defined between each corresponding pair of intermediate and outer support members 422 and 424, respectively, when in expanded and intermediate configurations. (As will be apparent to those of ordinary skill in the art, the size of such overlapping regions 436 varies depending on the degree of expansion.)

Each of the outer support members 424 preferably presents a single, distal hook 424h projecting upwardly from the top edge 424f and disposed inward of and adjacent the outer end 424e.

A longitudinally extending slot 424i is preferably defined through the body 424a of each outer support member 424. Each slot 424i presents a pair of proximal and distal ends 424j and 424k, respectively. Each slot defines a longitudinal slot length and a vertical slot height. The slot length most preferably approaches a total length of the outer support member 424. Each slot 424i is preferably disposed in a central portion of the body 424a (i.e., at least substantially equidistant from the top and bottom edges 424f and 424g, respectively).

A tab 424l preferably projects forward and at least substantially orthogonally relative to the corresponding front face 424b at each outer end 424e.

Preferably, the bodies 420a and 422a of the foundational and intermediate support members 420 and 422, respectively, are each at least substantially identically sized and shaped except as noted above. That is, a height of the foundational support member 420 defined between the top and bottom edges 420c and 420d thereof is preferably equal to similarly defined heights of the intermediate support members 422. Likewise, widths defined between ends 420b and between end 422d and 422e, respectively, are preferably equal.

In contrast, a similarly defined height of each outer support member 424 is most preferably about half that of the foundational support member 420 and of the intermediate support members 422. A similarly defined length of each outer support member 424 is preferably slightly less than (for instance, about ninety (90) percent) that of the foundational support member 420 and of the intermediate support members 422.

Figure 20:
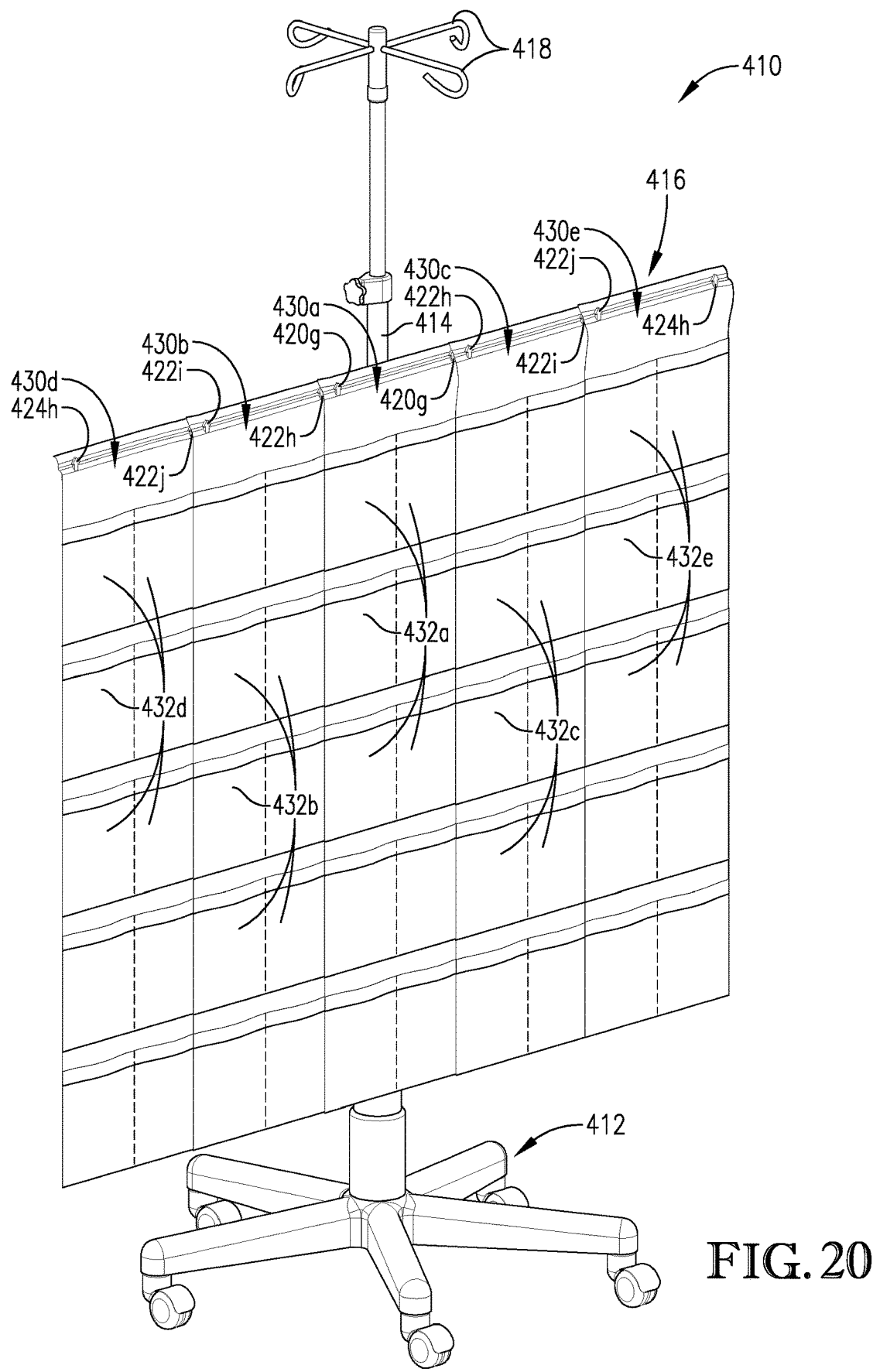
FIG. 20 is a front perspective view of a surgical sponge inventory rack according to a third preferred embodiment of the present invention, particularly illustrating a fully open or expanded configuration.
Figure 21:
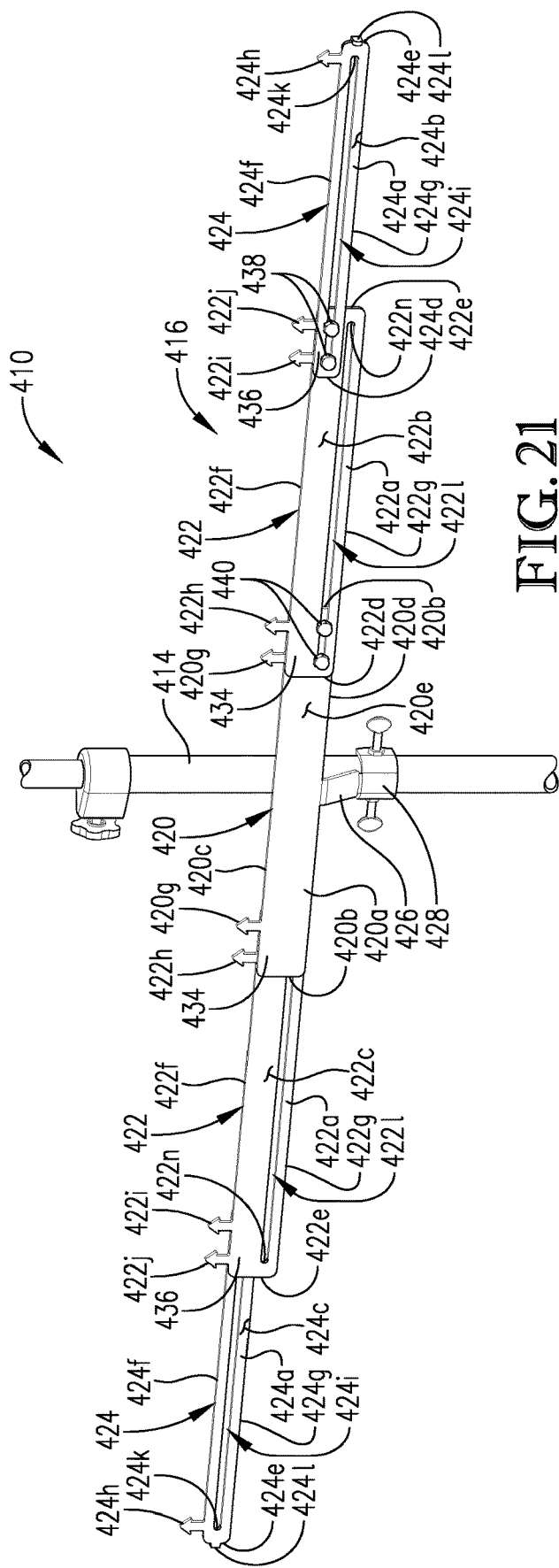
FIG. 21 is an enlarged front perspective view of a portion of the rack of FIG. 20, in a fully open or expanded configuration.

FIGS. 20 and 21 illustrate the rack 410 in its fully expanded configuration. The projections 422$k$ of each intermediate support member 422 extend through the corresponding slot 424$i$ in the corresponding outer support member 424 and thereby support the corresponding outer support member 424. An inner one of each pair of projections 422$j$ engages the inner end 424$j$ of the corresponding slot 424$i$ to restrict further outward motion of the outer support member 424. Dome nuts 438 are secured to the projections 422$k$ to restrict fore/aft shifting of the outer overlapped regions 436, as well as inadvertent relative lateral shifting (e.g., inadvertent collapse of the bag holder 416).

Similarly, the projections 420$h$ of the foundational support member 420 extend through corresponding ones of the slots 422$l$ in the corresponding intermediate support members 422 to support the corresponding intermediate support members 422. An inner one of each pair of projections 420$h$ engages the inner end 422$m$ of the corresponding slot 422$l$ to restrict further outward motion of the intermediate support member 422. Dome nuts 440 are secured to the projections 420$h$ to restrict fore/aft shifting of the overlapped regions 434, as well as inadvertent relative lateral shifting (e.g., inadvertent collapse of the bag holder 416).

It is noted that, in the fully expanded configuration, the intermediate and outer support members 422 and 424 are positioned such that the lengths of the inner and outer overlapping regions 346 and 436 are minimized to the extent possible (i.e., given the geometrical constraints of the support members 420, 422, and 424). That is, within the constraints of the geometry of the support members 420, 422, and 424, a collective lateral width or span achieved by the support members 420, 422, and 424 is maximized.

Figure 23:
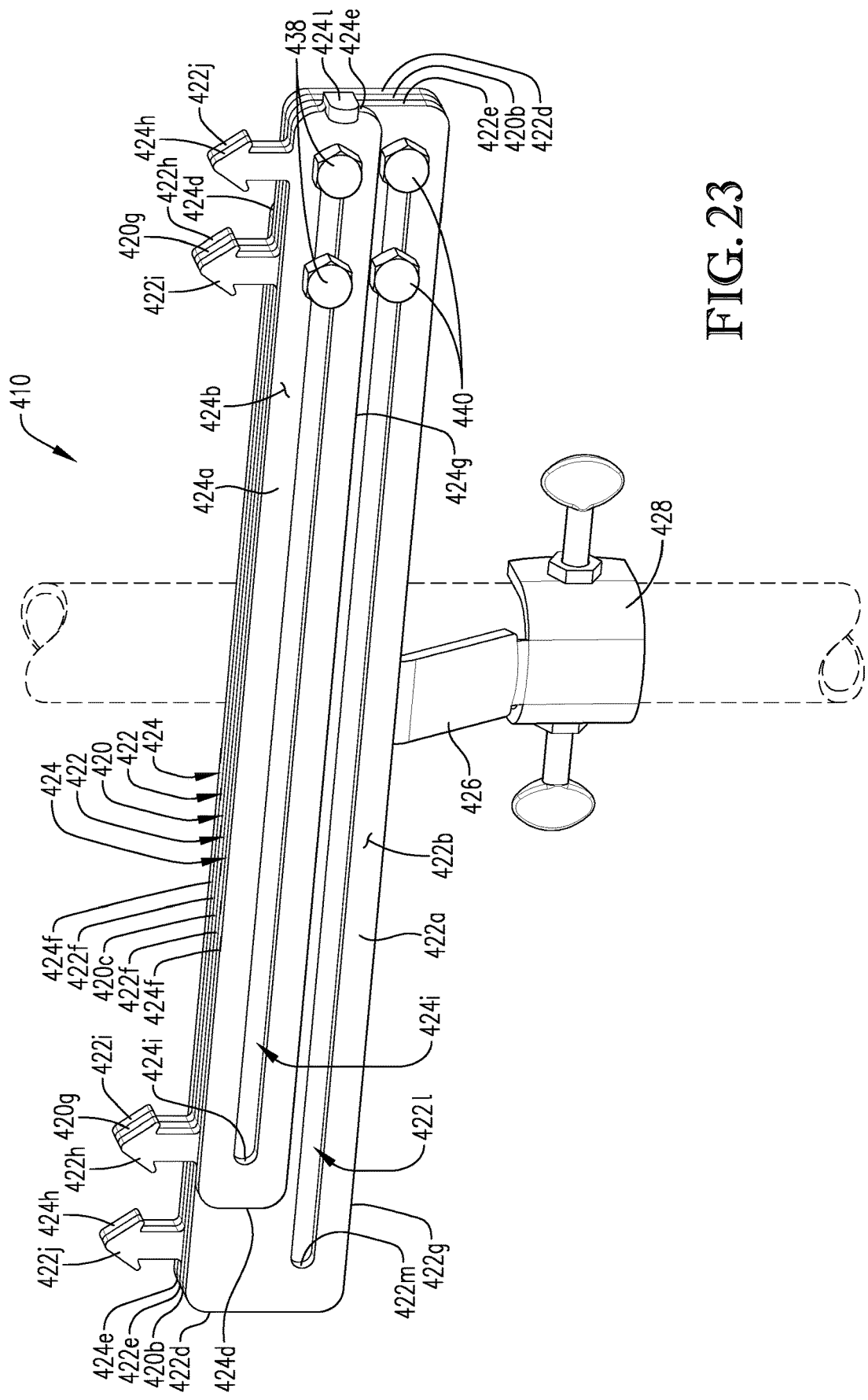
FIG. 23 is a front perspective view of the portion of the rack of FIGS. 21 and 22, in a fully contracted or closed configuration.

FIGS. 22 and 23 illustrates a preferred process of collapsing the rack 410 from the fully expanded configuration of FIG. 21, through intermediate stages such as that shown in FIG. 22, to a compact, fully contracted configuration best shown FIG. 23. First, if necessary, some or all of the dome nuts 438 and 440 are loosened. Most preferably, the nuts 438 and 440 are set so as to sufficiently restrict unintentional lateral shifting but facilitate intentional expansion or collapse without additional adjustment, making such a step unnecessary. However, adjustments may be made before, during, and/or after any of the steps in a collapsing or expanding process without departing from the scope of some aspects of the present invention.

Next, laterally inward shifting of the outer support members 424 relative to the (presently preferably stationary) intermediate support members 422 is initiated via pressure on the tabs 424$l$. In this example methodology, the application of force and the biasing of the dome nuts 438 and 430 is such that the outer support members 424 shift fully inwardly relative to the intermediate support members 422 without any laterally inward shifting of the intermediate support members 422 occurring. However, it is permissible according to some aspects of the present invention for shifting to occur simultaneously, either proportionally (e.g., at an equal rate) or non-proportionally (e.g., more slowly for the intermediate support members 422). Also, it is permissible for shifting to occur symmetrically or asymmetrically, or variably, as dictated by the forces applied, the biasing of the dome nuts 438 and 440 (so as to facilitate a preferred degree of friction between paired members 422 and 424), etc.

As shown in FIG. 22, upon completion of this step (and assuming shifting of the only the outer support members 424 has occurred), the outer of the projections 422$k$ (hidden from view underneath corresponding dome nuts 438) engage corresponding ones of the outer slot ends 424$k$, two (2) sets of hooks 422$j$ and 424$h$ overlie one another, and the bottom edge 424$g$ of each outer support member 424 is disposed adjacent the corresponding slot 422$l$ of the corresponding intermediate support member 422. Furthermore, the outer ends 422$e$ and 424$e$ align with one another, as do the top edges 422$f$ and 424$f$.

In a preferred methodology, simultaneous and proportional laterally inward shifting of the intermediate support members 422 and the outer support members 424 relative to the stationary foundational support member 420 is initiated next via continued pressure on the tabs 424$l$ and consequent transfer of force from each outer support member 424 to the corresponding intermediate support member 422 via the outer one of the respective projections 422$k$. This step ends with the rack 410 in a fully collapsed configuration, as shown in FIG. 23, with the support members 420, 422, and 424 forming a compact stack consisting of a foremost one of the outer support members 424, overlying a foremost one of the intermediate support members 422, overlying the foundational support member 420, overlying a rearmost one of the intermediate support members 422, overlying a rearmost one of the outer support members 424.

More particularly, upon completion of this step, the outer of the projections 422$k$ (topped by corresponding dome nuts 438) still engage corresponding ones of the outer slot ends 424$k$. Furthermore, the outer of the projections 420$h$ (topped by corresponding dome nuts 440) additionally engage corresponding ones of the outer slot ends 422$n$. Two (2) sets of hooks 422$j$ and 424$h$ still overlie one another; and two (2) additional sets of overlying hooks 420$g$, 422$i$, and 422$h$ are additionally formed (the hooks 422$i$ and 422$h$ in each overlying set of course being from different ones of the intermediate support members 422). As before, the bottom edge 424$g$ of each outer support member 424 is disposed adjacent and above the corresponding slot 422$l$ of the corresponding intermediate support member 422. The bottom edges 420$d$ and 422$g$ of the foundational and intermediate support members 420 and 422 align with one another, as do all of the top edges 420$c$, 422$f$, and 424$f$ of the foundational, intermediate, and outer support members 420, 422, and 424.

Still further, the outer ends 424$e$ and 422$e$ of the foremost outer and intermediate support members 424 and 422, respectively, align with corresponding ends 420$b$ of the foundational support member and with the inner end 422$d$ of the rearmost of the intermediate support members 422. The inner end 424$d$ of the rearmost outer support member 424 is disposed inward of the aforementioned aligned ends 424$e$, 422$e$, 420$b$, and 422$d$. Conversely, the outer ends 424$e$ and 422$e$ of the rearmost outer and intermediate support members 424 and 422, respectively, align with the other end 420$b$ of the foundational support member and with the inner end 422$d$ of the foremost of the intermediate support members 424. The inner end 424$d$ of the foremost outer support member 424 is disposed inward of the aforementioned aligned ends 424$e$, 422$e$, 420$b$, and 422$d$.

It is noted that the bodies 420$a$, 422$a$, and 424$a$ all extend parallel to one another in the fully expanded, fully contracted, and any intermediate configurations of the bag holder 416. This is in contrast to the rack 210 of the first preferred embodiment, in which the pivoting members 236*d* and 236*e* are not parallel with the remaining members 236*a*, 236*b*, and 236*d* during some stages of collapse.

In view of the above, it will be apparent that a collective fore-and-aft depth of the support members 420, 422, and 424 remains constant regardless of the degree of expansion thereof. That is, the depth of the support members 420, 422, and 424 in the fully contracted configuration, the fully expanded configuration, and any intermediate configurations remains constant.

The collective fore-and-aft depth of the support members 420, 422, and 424, including the tabs 4241, is preferably between about five tenths inches (0.5") and about three inches (3"). More preferably, the fore-and-aft depth is between about one inch (1") and about two inches (2"). Most preferably, the fore-and-aft depth is about one and three hundred eighty-five thousandths inches (1.385"). The bodies 420*a*, 422*a*, and 424*a* of the support members 420, 422, and 424 collectively present a constant depth of about five eighths inches (0.625").

Similarly to the rack 310 of the second preferred embodiment but in contrast to the rack 210 of the first preferred embodiment, a collective vertical height (i.e., along the direction of the rod axis) of the support members 420, 422, and 424 remains constant regardless of the degree of expansion thereof. That is, the collective height of the support members 420, 422, and 424 in the fully contracted configuration, the fully expanded configuration, and any intermediate configurations remains constant.

Most preferably, the collective height of the support members 420, 422, and 424, excluding the hooks 420*g*, 422*h*, 422*i*, 422*j*, and 424*h*, is between about one half inch (0.5") and about three inches (3"). More preferably, the height is between about one inch (1") and about two inches (2"). Most preferably, the height is about one and three eighths inches (1.375"). In greater detail still, each of the bodies 420*a* and 422*a* preferably has a height of about one and three eighths inches (1.375"). Each of the bodies 424*a* preferably has a height of about three quarters inches (0.75").

Still further, a collective lateral collapsed or contracted width or span of all of the support members 420, 422, and 424 is minimized when the rack 410 is in a fully contracted or collapsed configuration.

The collective collapsed width of all of the support members 420, 422, and 424, including the tabs 4241, is preferably between about five inches (5") and about twenty inches (20"). More preferably, the collapsed width is between about seven and five tenths inches (7.5") and about fifteen and five tenths inches (15.5"). Most preferably, the collapsed width is about eleven and five tenths inches (11.5").

Preferably, the expanded width is at least two (2) times the collapsed width. More preferably, the expanded width is at least three (3) times the collapsed width. Still more preferably, the expanded width is at least four (4) times the collapsed width. Most preferably, the expanded width is about four and five tenths (4.5) times the collapsed width.

The collective expanded width of all of the support members 420, 422, and 424, including the tabs 4241, is preferably between about twenty-five inches (25") and about sixty-five inches (65"). More preferably, the expanded width is between about thirty-five inches (35") and about fifty-five inches (55"). Most preferably, the expanded width is about forty-five and three quarters inches (45.75").

Preferably, each of the bodies 420*a* and 422*a* has a width of about eleven inches (11"). Each of the bodies 424*a* preferably has a width of about ten and one eighth inches (10.125").

Although the above-described method for collapsing the rack 410 is a preferred method, various other methods may be used, including methods in which the above-described steps are simply performed in a different order or in whole or partially simultaneously. For instance, as noted above, the initial shifting of the outer support members might be accompanied by at least some degree of shifting of the intermediate support members, one of the outer support members might move inward more rapidly than the other, etc. Application of necessary forces may also be to other components of the rack 410, not just to the tabs 4241 as described above, also resulting in various different sequences of movement.

Expansion of the rack 410 is preferably initiated with outward shifting of each of the outer support members 424 relative to the corresponding ones of the intermediate support members 422, which preferably remain stationary, as a result of force being applied to the tabs 4241.

When the inner end 424*j* of the slot 424*i* of each outer support member 242 engages the corresponding inner one of the projections 422*k* (beneath a corresponding dome nut 438) of the corresponding intermediate support member 242, continued force applied to the tabs 4241 results in transfer of force from each outer support member 424 to the corresponding intermediate support members 422 via the projections 422*k*. This results in outward shifting of both the outer support members 424 and the intermediate support members 422, with shifting of corresponding ones of the intermediate and outer support members 422 and 424 preferably occurring simultaneously and proportionally.

Outward shifting is complete when the inner ones of the projections 420*h* (beneath corresponding dome nuts 440) of the foundational support member 420 engage corresponding inner ends 422*m* of the slots 4221 of the intermediate support members 422. The inner ones of the projections 422*k* (beneath dome nuts 438) of the intermediate support members 422 also engage corresponding inner ends 424*j* of the slots 424*i* of the outer support members 424.

Although the above-described expansion methodology is preferred, numerous variations in expansion methodology are also permissible. For instance, although it is preferred that the intermediate support members 422 remain stationary during the initial inward shifting of the outer support members 424, proportional, non-proportional, and/or asymmetrical shifting might occur. Numerous other methodology variations permitted by the structure of the rack 414, including but not limited to analogs of those described above with regard to collapse, also fall within the scope of some aspects of the present invention.

It is noted that the height of each slot 4221 and 424*i* is preferably at least substantially equal and, more particularly, only slightly larger than the height (or, most preferably, diameter) of the corresponding projections 420*h* and 422*k*. This facilitates ease of relative sliding by the intermediate and outer support members 422 and 424. This also facilitates stable support of the intermediate support members 422 on the projections 420*h* of the foundational support member 420 and of the outer support members 424 on the projections 422*k* of the intermediate support members 422.

The design of the expandable and collapsible support rack 410 and, more specifically, the bag holder 416 described above is highly advantageous. For instance, the consistent height of the bag holder 416 in collapsed, expanded, and intermediate configurations facilitates its use in space-constrained areas. Its significant reduction in width through collapsing likewise provides advantages in cramped quarters, yet its span when partially or fully expanded enables significant numbers of pockets to be both easily accessible and easily viewable. Furthermore, its simple, sliding-only operation (i.e., without pivoting, turning, or other motions being necessary) provides for quick adjustments and general ease of use.

CONCLUSION

Although the above description presents features of preferred embodiments of the present invention, other preferred embodiments may also be created in keeping with the principles of the invention. Furthermore, as noted previously, these other preferred embodiments may in some instances be realized through a combination of features compatible for use together despite having been presented independently as part of separate embodiments in the above description.

The preferred forms of the invention described above are to be used as illustration only and should not be utilized in a limiting sense in interpreting the scope of the present invention. Obvious modifications to the exemplary embodiments, as hereinabove set forth, could be readily made by those skilled in the art without departing from the spirit of the present invention.

The inventor hereby states his intent to rely on the Doctrine of Equivalents to determine and assess the reasonably fair scope of the present invention as pertains to any apparatus not materially departing from but outside the literal scope of the invention as set forth in the following claims.

What is claimed is:

1. A surgical sponge inventory rack comprising:
a mounting rod extending in a vertical direction;
a sponge bag holder connected to the mounting rod and projecting relative thereto in a lateral direction that is transverse to the vertical direction; and
a sponge bag supported on the sponge bag holder and including a pocket configured to receive and display a surgical sponge,
said sponge bag holder including a plurality of support members,
said support members being shiftable relative to one another to transition the sponge bag holder between a collapsed configuration and an expanded configuration,
at least one of said support members extending in the lateral direction past another of said support members when the sponge bag holder is in the expanded configuration,
said support members collectively presenting a depth in a fore-and-aft direction that is transverse to the lateral direction and transverse to the vertical direction,
said depth being at least substantially constant as the sponge bag holder transitions between the collapsed configuration and the expanded configuration.

2. The surgical sponge inventory rack of claim 1,
said support members collectively presenting a lateral collapsed width when the sponge bag holder is in the collapsed configuration and collectively presenting a lateral expanded width when the sponge bag holder is in the expanded configuration,
said expanded width being at least three times said collapsed width.

3. The surgical sponge inventory rack of claim 1,
each of said support members being slidably intercoupled with an adjacent one of said support members.

4. The surgical sponge inventory rack of claim 3,
each of said support members including a laterally extending body,
a first one of said support members including a projection extending from the body thereof in the fore-and-aft direction,
a second one of said support members being disposed adjacent said first one of the support members,
said body of the second one of the support members defining a laterally extending slot therethrough,
said projection extending into said slot, such that lateral shifting of the first and second ones of the support members relative to one another results in sliding of the projection within the slot.

5. The surgical sponge inventory rack of claim 4,
said slot presenting a laterally innermost end,
said projection engaging said laterally innermost end when the sponge bag holder is in the expanded configuration.

6. The surgical sponge inventory rack of claim 1,
each of said support members including a laterally extending body,
said bodies extending at least substantially parallel to one another when the sponge bag holder is in the collapsed configuration and when the sponge bag holder is in the expanded configuration.

7. The surgical sponge inventory rack of claim 6,
said bodies additionally extending at least substantially parallel to one another when the sponge bag holder is in any of a plurality of intermediate configurations formed transitorily between said collapsed configuration and said expanded configuration.

8. The surgical sponge inventory rack of claim 1,
said support members including a foundational support member, a pair of intermediate support members, and a pair of outer support members,
each of said intermediate support members being disposed between the foundational support member and a corresponding one of the outer support members.

9. The surgical sponge inventory rack of claim 8,
said foundational support member being fixed relative to the mounting rod to be laterally immovable relative thereto.

10. The surgical sponge inventory rack of claim 1,
said sponge bag holder configured such that each of said support members is disposed forward of the mounting rod when the sponge bag holder is in the collapsed configuration, the expanded configuration, and transitioning therebetween.

11. The surgical sponge inventory rack of claim 1,
at least one of said support members supporting the sponge bag when the sponge bag holder is in the expanded configuration.

12. The surgical sponge inventory rack of claim 11,
said at least one of said support members including a laterally extending body and a hook extending therefrom,
said hook supporting the sponge bag.

13. A method of storing and displaying used surgical sponges on a surgical sponge inventory rack, wherein said surgical sponge inventory rack includes a mounting rod extending in a vertical direction and a sponge bag holder connected to the mounting rod, said sponge bag holder including a plurality of support members, said method comprising the steps of:

(a) shifting the support members relative to one another in a lateral direction that is transverse to the vertical direction, such that at least one of the support members extends in the lateral direction past another of the support members, to transition the sponge bag holder from a collapsed configuration to an expanded configuration;

(b) hanging a sponge bag from one of said support members such that a pocket of the sponge bag is visible on a front side of the surgical sponge inventory rack; and (c) placing a used sponge into said pocket such that the used sponge is visible from the front side of the surgical sponge inventory rack.

14. The method of claim 13, said support members collectively presenting a depth in a fore-and-aft direction that is transverse to the lateral direction and transverse to the vertical direction, said depth being at least substantially constant during the course of each of steps (a), (b), and (c).

15. The method of claim 13, said support members collectively presenting a height in the vertical direction, said height being at least substantially constant during the course of each of steps (a), (b), and (c).

16. The method of claim 13, said support members collectively presenting a width in the lateral direction, step (a) including the step of expanding the width from a collapsed width to an expanded width that is at least three times the collapsed width.

17. The method of claim 13, step (a) including the step of sliding the support members relative to one another in the lateral direction.

18. The method of claim 13, each of said support members including a laterally extending body, said bodies extending at least substantially parallel to one another during the course of each of steps (a), (b), and (c).

19. The method of claim 13, further comprising the steps of:

(d) after step (b) and before step (c), hanging one or more additional sponge bags from corresponding ones of said support members such that respective pockets of the one or more additional sponge bags are visible on the front side of the surgical sponge inventory rack; and (e) after step (c), placing one or more additional used sponges into corresponding ones of said respective pockets of the one or more additional sponge bags, such that all of said used sponges are visible on the front side of the surgical sponge inventory rack.

\* \* \* \* \*